(12) United States Patent
Jermy et al.

(10) Patent No.: US 10,525,023 B2
(45) Date of Patent: *Jan. 7, 2020

(54) HIERARCHICAL SILICEOUS MESOSILICALITE NANOCARRIER

(71) Applicant: Imam Abdulrahman Bin Faisal University, Dammam (SA)

(72) Inventors: B. Rabindran Jermy, Dammam (SA); Vijaya Ravinayagam, Dammam (SA)

(73) Assignee: Imam Abdulrahman Bin Faisal University, Dammam (SA)

(*) Notice: Subject to any disclaimer, the term of this patent is extended or adjusted under 35 U.S.C. 154(b) by 107 days.

This patent is subject to a terminal disclaimer.

(21) Appl. No.: 15/478,794

(22) Filed: Apr. 4, 2017

(65) Prior Publication Data

US 2018/0280303 A1   Oct. 4, 2018

(51) Int. Cl.
| | |
|---|---|
| *B01J 20/34* | (2006.01) |
| *A61K 31/192* | (2006.01) |
| *C01B 37/00* | (2006.01) |
| *B01J 20/10* | (2006.01) |
| *B01J 20/28* | (2006.01) |
| *B01J 20/30* | (2006.01) |
| *A61K 9/51* | (2006.01) |

(52) U.S. Cl.
CPC .......... *A61K 31/192* (2013.01); *A61K 9/5115* (2013.01); *A61K 9/5192* (2013.01); *B01J 20/10* (2013.01); *B01J 20/2808* (2013.01); *B01J 20/28071* (2013.01); *B01J 20/28073* (2013.01); *B01J 20/28076* (2013.01); *B01J 20/28083* (2013.01); *B01J 20/3057* (2013.01); *B01J 20/3078* (2013.01); *C01B 37/005* (2013.01); *C01P 2002/60* (2013.01); *C01P 2006/10* (2013.01); *C01P 2006/12* (2013.01); *C01P 2006/14* (2013.01); *C01P 2006/16* (2013.01)

(58) Field of Classification Search
None
See application file for complete search history.

(56) References Cited

U.S. PATENT DOCUMENTS

| | | | |
|---|---|---|---|
| 7,678,955 B2 | 3/2010 | Martens et al. | |
| 8,617,513 B2 | 12/2013 | Ying et al. | |
| 8,951,498 B2 | 2/2015 | Larsen et al. | |
| 2010/0291387 A1* | 11/2010 | Chaumonnot | C01B 33/46 428/402 |

FOREIGN PATENT DOCUMENTS

| | | |
|---|---|---|
| CN | 104546804 A | 4/2015 |
| EP | 2 584 913 A1 | 5/2013 |
| IN | 20110073011 | 10/2012 |
| WO | WO 2014/060080 A1 | 4/2014 |

OTHER PUBLICATIONS

Vilaça, N., et al., J. Phys. Chem. 119: 3589-3595 (2015). (Year: 2015).*
S. Iraji, et al., "Functionalized Mesoporous Silica Nanoparticles as a Novel Antioxidant Delivery System", Iranian Journal of Chemical Engineering, vol. 12, No. 4, 2015, pp. 93-100.
Haifeng Hu, et al., "Preparation, characterization and in vitro release study of gallic acid loaded silica nanoparticles for controlled release", Pharmazie, vol. 68, No. 6, Jun. 2013, pp. 401-405.
Ladan Rashidi, et al., "A cellular uptake and cytotoxicity properties study of gallic acid-loaded mesoporous silica nanoparticles on Caco-2 cells", Journal of Nanoparticle Research, vol. 16, No. 2285, Mar. 2014, 14 pages.

* cited by examiner

Primary Examiner — David J Blanchard
Assistant Examiner — Daniel F. Coughlin
(74) Attorney, Agent, or Firm — Oblon, McClelland, Maier & Neustadt, L.L.P.

(57) ABSTRACT

A mesosilicalite nanocarrier having a hierarchical silicalite characterized by a molar ratio of aluminum to silica in a range of 1:3000 to 1:1000. The hierarchical silicalite includes mesopores of a hexagonal structure, and micropores of silicalite structure with a microporous volume in the range of 0.05 cc/g to 0.1 cc/g. The nanocarrier has a mesophase content in the range of 30 wt % to 70 wt %, a microphase content in the range of 30 wt % to 70 wt %, and a mean pore diameter in the range of 1.5 nm to 5.5 nm. A method of preparing the stable mesosilicalite nanocarrier with hierarchical micro/mesopores to load an antioxidant or drug for targeted drug delivery is also described.

3 Claims, 21 Drawing Sheets

Gallic acid control

Gallic acid deposition over 1D Q10 silica

Gallic acid dispersion in Q10 silica

C Kα1_2

250μm

Gallic acid dispersion in mesosilicalite

C Kα1_2

50μm

HIERARCHICAL SILICEOUS MESOSILICALITE NANOCARRIER

BACKGROUND OF THE INVENTION

Technical Field

The present invention relates to a hierarchical mesosilicalite nanocarrier capable of being loaded with antioxidant or therapeutic drugs for targeted drug delivery in treatment of cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Cancer is an uncontrolled and abnormal growth of the cell stimulated by mutation. Cancer initially arises from a single cell and then transforms into malignant cells. The cancer includes different stages, namely progression, precancerous lesion, and malignant tumor. These changes are easily promoted by the interaction of individual genetic factors with an external agent. Cancers caused the death of about 8.2 million people in 2012. See L. A. Torre, F. Bray, R. L. Siegel, J. Ferlay, J. Lortet-Tieulent, A. Jemal, Global Cancer Statistics, 2012, CA CANCER J CLIN 2015; 65:87-108, incorporated herein by reference in its entirety. Free radicals are unpaired electrons that induce oxidative stress in cells leading to metabolic changes in cells. The oxidative stress caused by an imbalance between oxidants and antioxidants in cells leads to damage. See Sies H. Oxidative stress: oxidants and antioxidants, Exp Physiol. 1997 March; 82(2): 291-5, incorporated herein by reference in its entirety. Sengottuvelan et al., [2009] reported that free radicals are scavenged by antioxidants and inhibit the cell damage. Neoplastic processes protect the cell from damage caused by free radicals. See M. Sengottuvelan, K. Deeptha, N. Nalini, Chemico-Biological Interactions, Volume 181, Issue 2, 7 Oct. 2009, Pages 193-201, incorporated herein by reference in its entirety. Thus antioxidants are vital in deterrence of various diseases. See I. S. Young, J. V. Woodside, Antioxidants in health and disease, J Clin Pathol 2001; 54:176-186, incorporated herein by reference in its entirety. Intensive research in free radical induced cytotoxicity has suggested that it may directly or indirectly be involved in cancer. See K. Rahman, Studies on free radicals, antioxidants, and co-factors, Clin Interv Aging. 2007 June; 2(2): 219-236, incorporated herein by reference in its entirety. A flourishing anticancer drug has to kill or debilitate cancer cells without causing damage to normal cells. Ravinayagam et al. [2012], characterized the role of Tridham (combinational herbal drug) on both Aflatoxin B1 induced hepatocellular carcinoma and Human hepatoma cell line (HepG2). See Vijaya Ravinayagam, R. Jaganathan, S. Panchanadham, S. Palanivelu. International Journal of Hepatology—Volume 2012, Article ID 428373, 9 pages, incorporated herein by reference in its entirety. The antioxidant and anticarcinogenic effect of a particular herbal preparation are derived by the synergistic activity of principal compounds (including gallic acid) present in the drug. Ravinayagam et al. [2012] isolated and elucidated one of the component gallic acid from Tridham crude extract (TD) through various physico-chemical techniques. See Vijaya Ravinayagam, R. Jaganathan, S. Panchanadham, S. Palanivelu. International Journal of Drug Discovery and Herbal Research, 2(2): April-June: (2012), 371-385, incorporated herein by reference in its entirety.

Chemotherapeutic treatment of cancer has been a disappointment due to resistance to chemotherapy and a need to deliver sufficient doses of an appropriate drug to the tumor. See Bruix J, Llovet J M, Hepatology. 2002 March; 35(3): 519-24, incorporated herein by reference in its entirety. In recent years, the development of medicine and nanotechnology (nanomedicine) has broadened the scope for effective and efficient therapies for deadly diseases such as cancer. The available nanotherapeutics overcome the limitations of current drug therapy (conventional), namely untargeted drug release, low bioavailability, and low therapeutic index. Nanomedicines take advantage of the tumor acidic microenvironment for effective drug release. Some nanoparticles have the ability of controlled capture or filling, transport, and release of drug molecules. The nanoparticles (carriers) carrying drugs have been shown to enter into the damaged epithelial layer of tumor cells and remain close to the tumor cells. Under such unique tumor acidic condition, the nanotherapeutics are shown to behave like a drug-supplying agent, which releases drugs in a continuous and sustainable manner. The ability to release drugs in a tumor environment makes nanotherapeutics more target specific, efficient, able to differentiate healthy cells, and thus induce fewer side effects. Among the technologies, nanoporous silica based drug delivery systems are proposed to be promising systems. See M. Vallet-Regi, F. Bala, D. Arcos, Angew. Chem. Int. Ed. 46 (2007) 7548-7558; and B. G Trewyn, I. I. Slowing, S. Giri, H-T. Chen, V-Y. Lin, Acc. Chem. Res. 40 (2007) 846-853, each incorporated herein by reference in their entirety. For the past decade, intense research has been focused on developing different structured mesoporous molecular sieves. The attractive features of such materials include high surface area, and unique and designable pore structures with uniformity. See M. M. Wan, X. D. Sun, S. Liu, J. Ma, J. H. Zhu, Micropor. Mesopor. Mater. 199 (2014) 40-49, incorporated herein by reference in its entirety. The possibility of designing the pore architecture such as one-dimensional (1D), two-dimensional (2D), and three-dimension (3D) based on the synthesis condition and mesoporous templates, makes them an attractive candidate as drug hosts (carrier) for drug delivery. The ordered mesostructures with tunable pore sizes offer excellent opportunity to load different molecular sizes of drugs of pharmaceutical interest within the pore network.

The 1D silica has a hollow morphology that can be filled with desired drug molecules. The cylindrical type silica offers many advantages such as tunable pore diameter, adjustable inner wall thickness (depending upon the thickness of templates) for high payload of drugs, easy functionalization both at interior and outer surface, and easy scale up for commercialization. The unique hollow tube structure may safeguard an antioxidant and therefore remains a potential drug delivery candidate, drug/gene delivery, bio membrane separation, etc. See X. Yang, H. Tang, K. Cao, H. Song, W. Sheng, Q. Wu, J. Mater. Chem., 21 (2011) 6122, incorporated herein by reference in its entirety. The 2D nanoporous silica are hexagonal structured materials (hexagonal MCM-41, SBA-15, and HMS) and are interesting due to their admirable physical characteristics including large surface area (200-1000 $m^2/g$), pore volume (>1.0 $cm^3/g$), and adjustable pore sizes (1-50 nm). See Kresge C T, Leonowicz M E, Roth W J, Vartuli J C, Beck J S, Nature 359 (1992)710-712; A. Sayari, Chem. Mater. 8 (1996)

1840-1852; and K. Moller, T. Bein, Chem. Soc. Rev., 42 (2013) 3689, each incorporated herein by reference in their entirety. The nanosilicas can be synthesized with particle sizes and exhibit high steam and hydrothermal stability. Such types of silicas have been used as possible drug delivery agents [Vallet-Regi et al., 2007]. Unlike conventional drug carriers (capsules, liposomes, viruses, and micelles), 2D nanosilica are stable against biochemical and bioerosions. The 2D mesopores are reported to be effective for ibuprofen and other related drugs. See M. Manzano, V. Aina, C. O. Arean, F. Balas, V. Cauda, M. Collila, M. R. Delgado, M. V. Regi, Chem. Eng. J. 137 (2008) 30-37, incorporated herein by reference in its entirety. However, the 2D materials have low hydrothermal stability due to amorphous frameworks accompanied with thin pore walls. 3D nanoporous silicas are multidirectional systems, where pores are connected with its eight nearest members through pore openings and produces a remarkable array of shapes such as MFI, SBA-16, MCM-48 etc. under basic and acidic synthesis conditions (Kresge et al., 1992, Sayari, 1996, Moller and Bein 2013). Cubic cage type structured silicas were reported by Sakamoto et al. [2000]. See Y. Sakamoto, M. Kneda, O. Terasaki, D. Y. Zhao, J. M. Kim, G. D. Stucky, H. J. Shin, R. Ryoo, Nature 408 (2000) 449, incorporated herein by reference in its entirety. The unique three-dimensional pore ordering is reported to provide easy access for entering molecules without diffusion resistance. Kleitz et al. [2006] used a low acid concentration along with additive solvent n-butanol for SBA-16 silica mesophase formation. See F. Kleitz, T.-W. Kim, R. Ryoo, Langmuir 22 (2006) 440, incorporated herein by reference in its entirety. The advantage of such SBA-16 mesotypes includes the presence of thick walls that helps to provide thermal and mechanical stabilities over two dimensional MCM-41 silica. Reports are available for using 3D type materials used for drug delivery applications with pharmaceutics such as ibuprofen, atenolol, and mefenamic acid. See M. Naghiloo, M. Yousef, M. S. Nourbakhsh, Z. Taherian, Journal of Sol-Gel Science and Technology, 74 (2015) 537-543; G. F. Andrade, D. C. F. Soares, R. K. Almeida, E. M. B. Sousa, Journal of Nanomaterials, 2012 (2012) 816496; and F M Mustafa, H. A Hodali, Materials Science and Engineering 92 (2015) 012018, each incorporated herein by reference in their entirety. To date, a variety of mesoporous materials have shown the potential drug adsorption and release capabilities. The drug captivation and release capabilities are unique and varies depending on the pore architectures. If mesoporous silica have 2D pore systems (ex. MCM-41 and SBA-15), the drug delivery are found to be high due to easy release from straight channels. See S. C. Shen, W. K. Ng, L. Chia, J. Hu, R. B. Tan, Int. J. Pharm. 410 (2011) 188-195, incorporated herein by reference in its entirety. However, if the silica have cubic structure such as MCM-48, the drug takes longer time to diffuse and release due to hindered three dimensional pore system. Therefore a new strategy is needed to develop materials which combine the advantages of large pores similar to mesoporus molecular sieves and small pores similar to that of zeolites. Pinnavaia et al. [2000] reported top-down approach, where parent ZSM-5 was transformed into mesostructured form with the inclusion of five-ring subunits of zeolite fragments in the presence of mesopore directing template. Kaliaguine reported a new approach (bottom-up approach), where using dilute seed solution of zeolite, he reported the formation of mesoporous aluminosilicates (ZCMesoAS) along with primary zeolite units. In our earlier publications, we reported the acidic type micropore and mesoporous ZSM-5 synthesized through top-down approach for petrochemical applications See R. J. Balasamy, T. Odedairo, S. Al-Khattaf, Appl. Catal. A: Gen., Vol. 409-410, 2011, 223-233; W. Alabi, L. Atanda, Rabindran Jermy, S. Al-Khattaf, Chem. Eng. Journal, 195-196 (2012) 276-288; R. J. Balasamy and S. Al-Khattaf, Catal. Sci. Technol., 2 (2012) 1275-1286; B. R. Jermy, M. A. B. Siddiqui, A. M. Aitani, M. R. Saeed, S. Al-Khattaf, J. Porous Mater. 19 (2012) 499-509; T. Odedairo, R. J. Balasamy, S. Al-Khattaf, J. Mol. Catal., 345 (2011) 21-36; and S. Al-Khattaf, T. Odedairo, R. J. Balasamy, Canadian Chemical Eng Journal, 9999 (2012) 1-11, each incorporated herein by reference in their entirety.

To date, the applications of an ordered non-acidic hierarchical micro/mesoporous material involving silicalite and SiMCM-41 composites have not been studied for drug adsorption and drug release study.

In view of the foregoing, an objective of the present invention is to provide a hierarchical mesosilicalite nanocarrier with mesopores and micropores that may be employed as a drug carrier for therapeutics by an equilibrium adsorption technique.

BRIEF SUMMARY OF THE INVENTION

According to a first aspect, the present disclosure relates to a mesosilicalite nanocarrier having a hierarchical silicalite which has a silica to aluminum molar ratio in a range of 1000:1 to 3000:1. The hierarchical silicalite includes mesopores of a hexagonal structure, and micropores of a microporous volume in the range of 0.05 cc/g to 0.1 cc/g. The nanocarrier has a mesophase content in the range of 30% to 70% relative to a total weight of the nanocarrier, a microphase content in the range of 30% to 70% relative to the total weight of the nanocarrier, and a mean pore diameter in the range of 1.5 nm to 5.5 nm.

In some embodiments of the mesosilicalite nanocarrier, the volume of the mesopores relative to a total weight of the nanocarrier is in the range of 0.11 cc/g to 1.5 cc/g.

In some embodiments of the mesosilicalite nanocarrier, the mesopores are ordered.

In some embodiments the mesosilicalite nanocarrier further includes an antioxidant loaded in the mesopores and/or micropores of the nanocarrier.

In some embodiments of the mesosilicalite nanocarrier, an adsorbed antioxidant weight is 10%-50% of a nanocarrier weight at an antioxidant loading rate in the range of 0.1 mmol/g of the nanocarrier to 16 mmol/g of the nanocarrier.

In some embodiments of the mesosilicalite nanocarrier, a total recovery yield for an antioxidant is in the range of 95% to 100% at an antioxidant loading rate in the range of 0.1 mmol/g of the nanocarrier to 1.0 mmol/g of the nanocarrier.

According to a second aspect, the present disclosure relates to a method of preparing the mesosilicalite nanocarrier from silicalite through a top down methodology. The mesosilicalite preparation includes mixing a silica source with a template to form a first mixture, and hydrothermally aging the first mixture at a temperature of 150° C.-200° C. for 24 hours to 86 hours to produce an aged first mixture. Drying the aged first mixture forms a silicalite, which is then treated with an alkaline solution and a surfactant to form a second mixture (containing a SiMCM-41/silicalite composite, for example). Hydrothermally aging the second mixture at a temperature of 60° C.-120° C. for 12 hours to 36 hours at a rate of 3° C./min to 6° C./min produces an aged second mixture. This is followed by neutralizing a pH of the aged second mixture, and a subsequent hydrothermal aging of the aged second mixture at a temperature of 60° C.-120° C. for 12 hours to 36 hours at a rate of 3° C./min to 6° C./min to produce a third mixture. Drying the third mixture forms the mesosilicalite nanocarrier.

In some implementations of the method, the silica source for silicalite preparation is colloidal silica.

In some implementations of the method, the colloidal silica has a surface area in the range of 120 m²/g to 150 m²/g.

In some implementations of the method, the colloidal silica has a density in the range of 1.15 g/mL to 1.35 g/mL at 25° C.

In some implementations of the method, the silicalite is a crystal having a crystal size of 1 μm to 5 μm.

In some implementations, the method further includes a calcining of the silicalite after the first drying, wherein the calcining takes place at a temperature in the range of 545° C.-605° C. for 5 hours to 11 hours and at a rate of 3° C./min to 6° C./min.

In some implementations, the method further includes a second calcining of the second mixture in a temperature range of 545° C.-605° C. after the drying.

In some implementations of the method, the template is tetrapropylammonium hydroxide.

In some implementations of the method, the surfactant is at least one of an alkylammonium halide or an alkylammonium hydroxide.

In some implementations of the method, the surfactant is cetyl trimethylammonium bromide.

In some implementations of the method, the alkaline solution comprises a base selected from the group consisting of sodium hydroxide, potassium hydroxide, lithium hydroxide, and barium hydroxide in a concentration range of 0.1 M to 0.8 M.

In some implementations of the method, the alkaline solution consists of sodium hydroxide in water at a concentration of 0.2 M to 0.7 M.

In some implementations, the method further includes loading the antioxidant into the mesosilicate nanocarrier, the loading including drying the mesosilicate nanocarrier at 100° C.-120° C. for 72 hours to 86 hours and mixing the dried mesosilicate nanocarrier with a solution of the antioxidant for 12 hours to 36 hours at 23° C.-30° C. to form the mesosilicate nanocarrier loaded with the antioxidant at 10% to 50% by weight of the total weight of the mesosilicate nanocarrier.

In some implementations of the method, the solution of the antioxidant is an acidic aqueous solution (for example, an acidic solution having a pH ~3).

In some implementations of the method, the antioxidant in the solution has a concentration of 0.25 g/L to 15 g/L.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
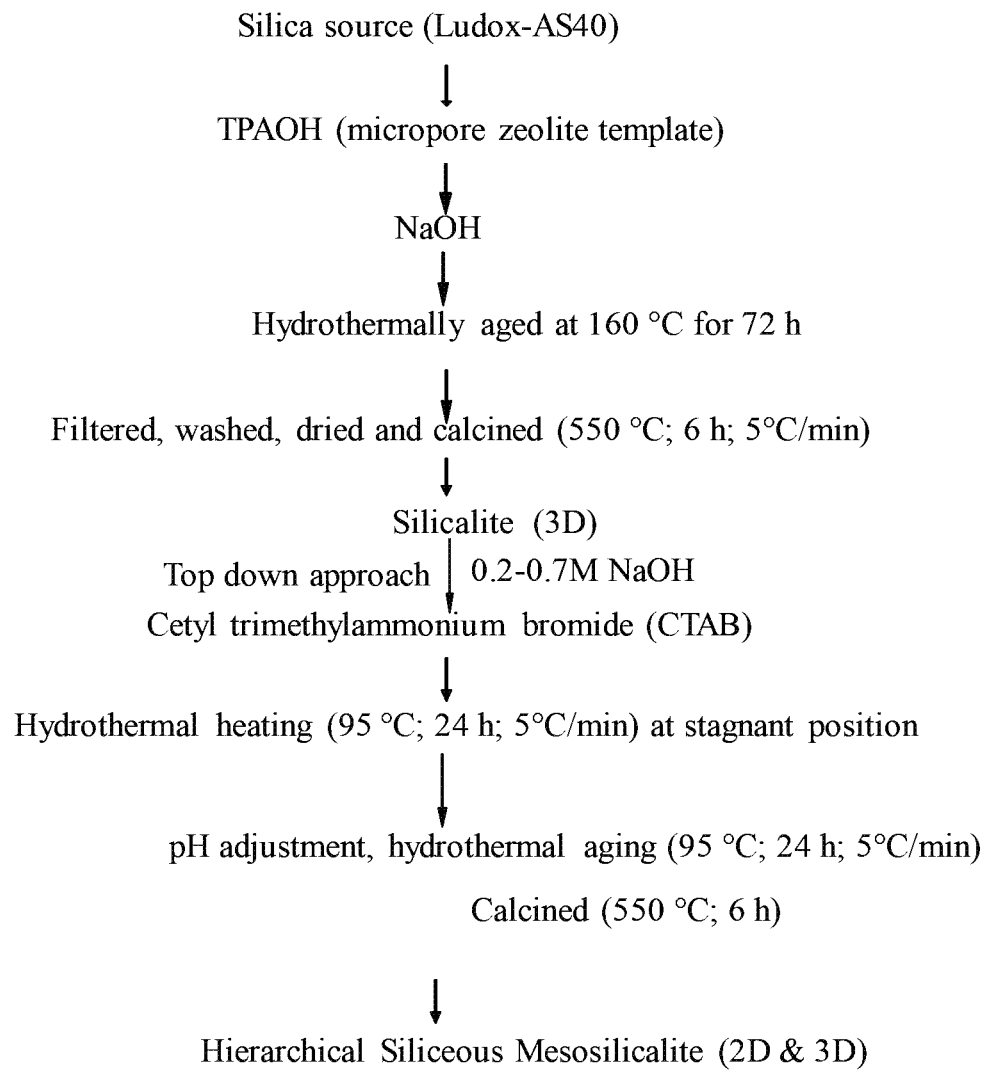
FIG. 1 is an exemplary flow chart of a method of preparing a mesosilicalite nanocarrier (SiMCM-41/silicalite composite) from a silicalite source using top-down methodology.

Referring now to the drawings, wherein like reference numerals designate identical or corresponding parts throughout the several views.

According to a first aspect, the present disclosure relates to a mesosilicalite nanocarrier having a hierarchical silicalite characterized by a molar ratio of silica to aluminum in a range of 1000:1 to 3000:1, or 1500:1 to 2500:1. An exemplary flow chart of the preparation of the mesosilicalite nanocarrier is depicted in FIG. 1 and described herein. The materials, reaction conditions (time, concentration, temperature, etc.) in FIG. 1 are exemplary and are not intended to limit the scope of the disclosure. The mesosilicalite nanocarrier may be interchangeably referred to as "nanocarrier" throughout the disclosure.

Figure 2:
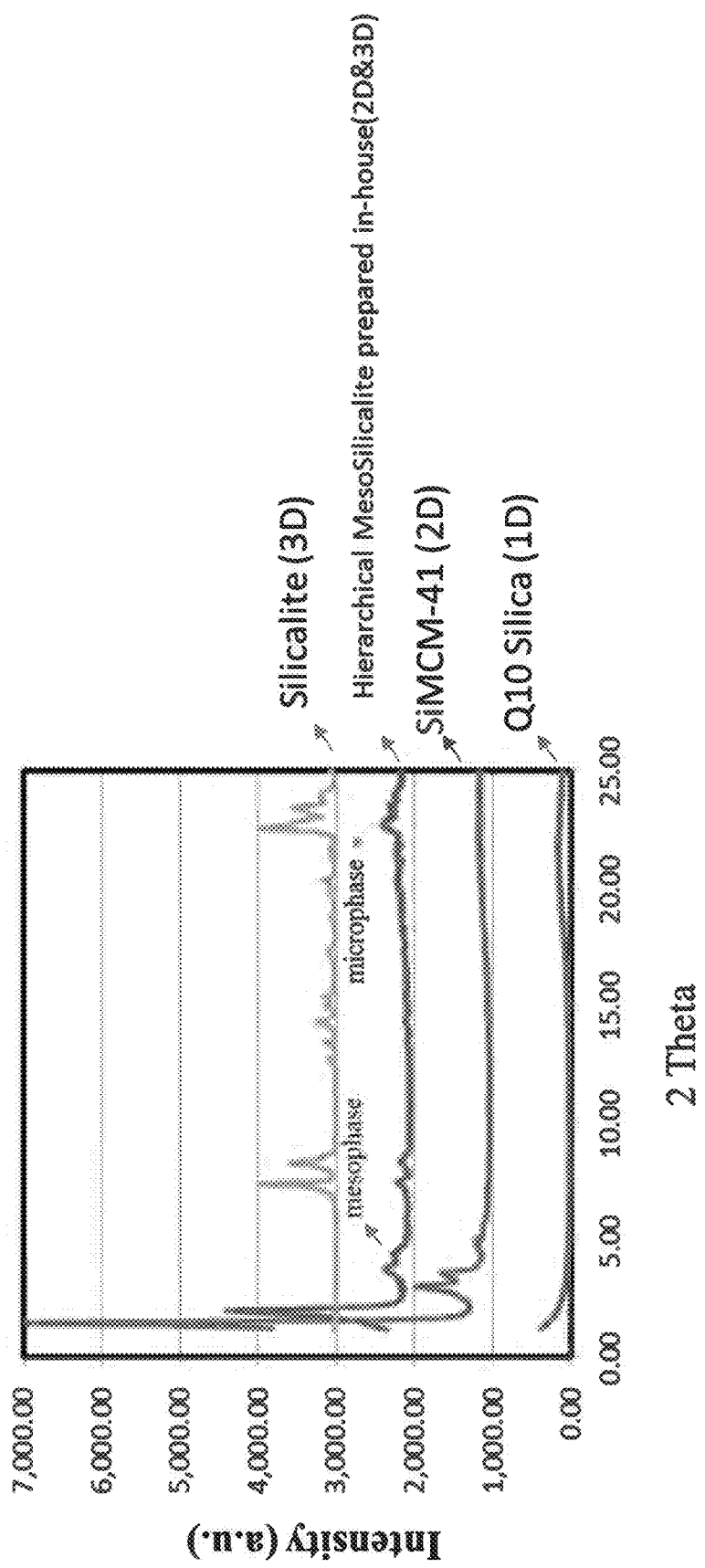
FIG. 2 is an X-Ray diffraction spectrum of silicalite, hierarchical mesosilicalite prepared, SiMCM-41, and Q10 silica.

Silicalite is a polymorph of silica having a structure analogous to zeolite. The presently described hierarchical silicalite includes mesopores of a hexagonal structure, and micropores of a microporous volume in the range of 0.05 cc/g to 0.1 cc/g, 0.06 cc/g to 0.09 cc/g, or 0.07 cc/g to 0.08 cc/g. FIG. 2 depicts an X-ray diffraction (XRD) spectrum of the mesosilicalite of the present disclosure in comparison to SiMCM-41, which is known to have hexagonal structure and non-hexagonally structured silicalite, and a silica. The XRD pattern indicates that the nanocarrier exhibits a hexagonal mesoporous form (at low angle of 2 theta) and silicalite form (at high angle of 2 theta). The hexagonal structure may be described as well-ordered and comparable in structure to MCM-41 mesoporous material as described by Kresge et al. (1992), Sayari, et al. (1996), and Moller, et al. (2013). See Kresge C T, Leonowicz M E, Roth W J, Vartuli J C, Beck J S, Nature 359 (1992)710-712; 15; A. Sayari, Chem. Mater. 8 (1996) 1840-1852; and K. Moller, T. Bein, Chem. Soc. Rev., 42 (2013) 3689, each incorporated herein in their entirety. In some embodiments of the mesosilicalite nanocarrier, the mesopores are of a mesoporous volume in the range of 0.11 cc/g to 1.5 cc/g, 0.15 cc/g to 1.25 cc/g, 0.25 cc/g to 1 cc/g, or 0.5 cc/g to 0.75 cc/g. The mesopores and micropores for the nanocarrier characterize the hierarchical structure of the mesosilicalite, wherein the mesopores form the mesophase and the micropores form the microphase. The relative weight ratios of these two phases approximates the relative weight ratios of the SiMCM-41 and silicalite used in the synthesis.

Figure 3:
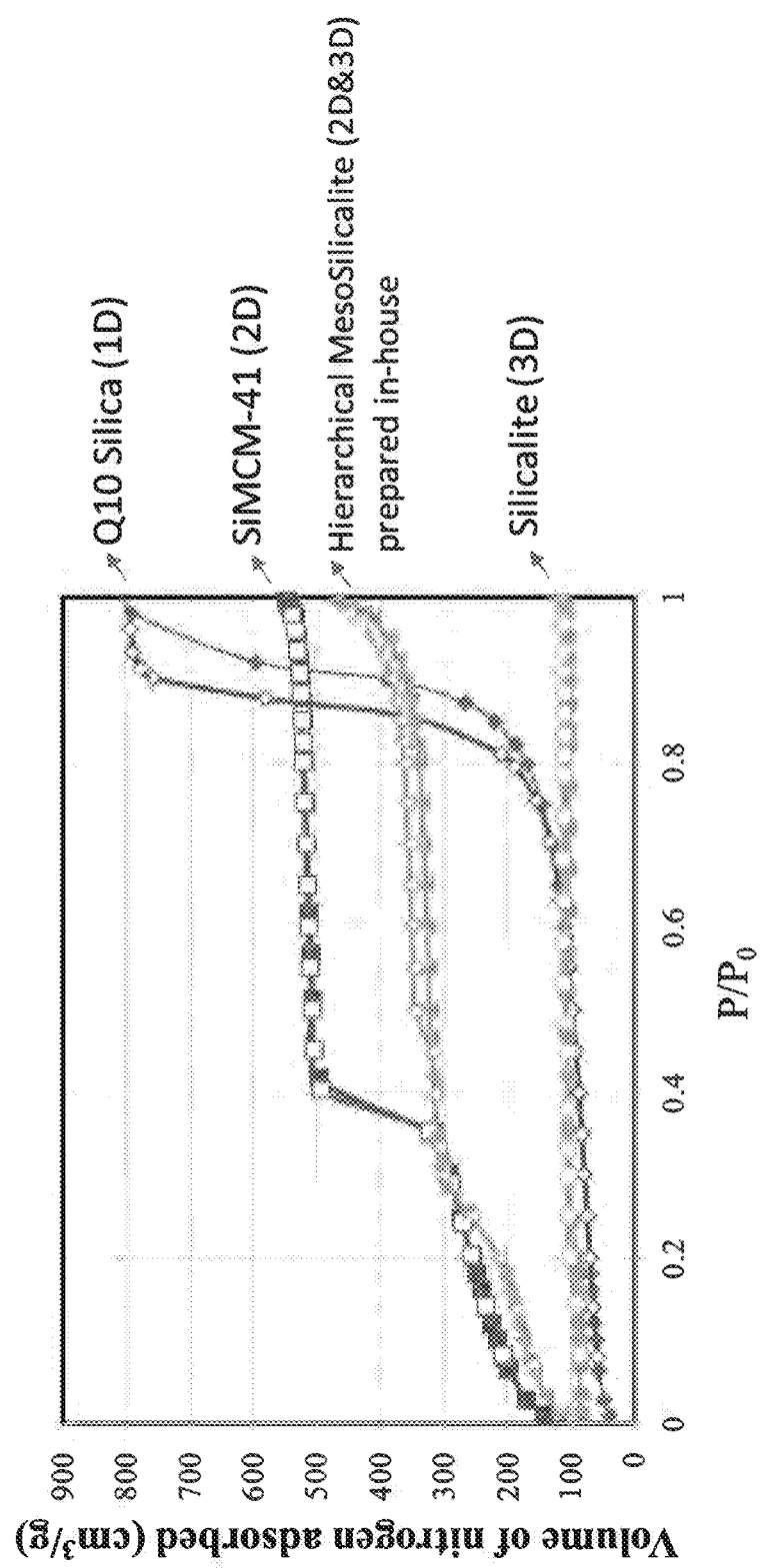
FIG. 3 is a nitrogen adsorption isotherm of Q10 silica, SiMCM-41, hierarchical mesosilicalite, and silicalite.
Figure 4:
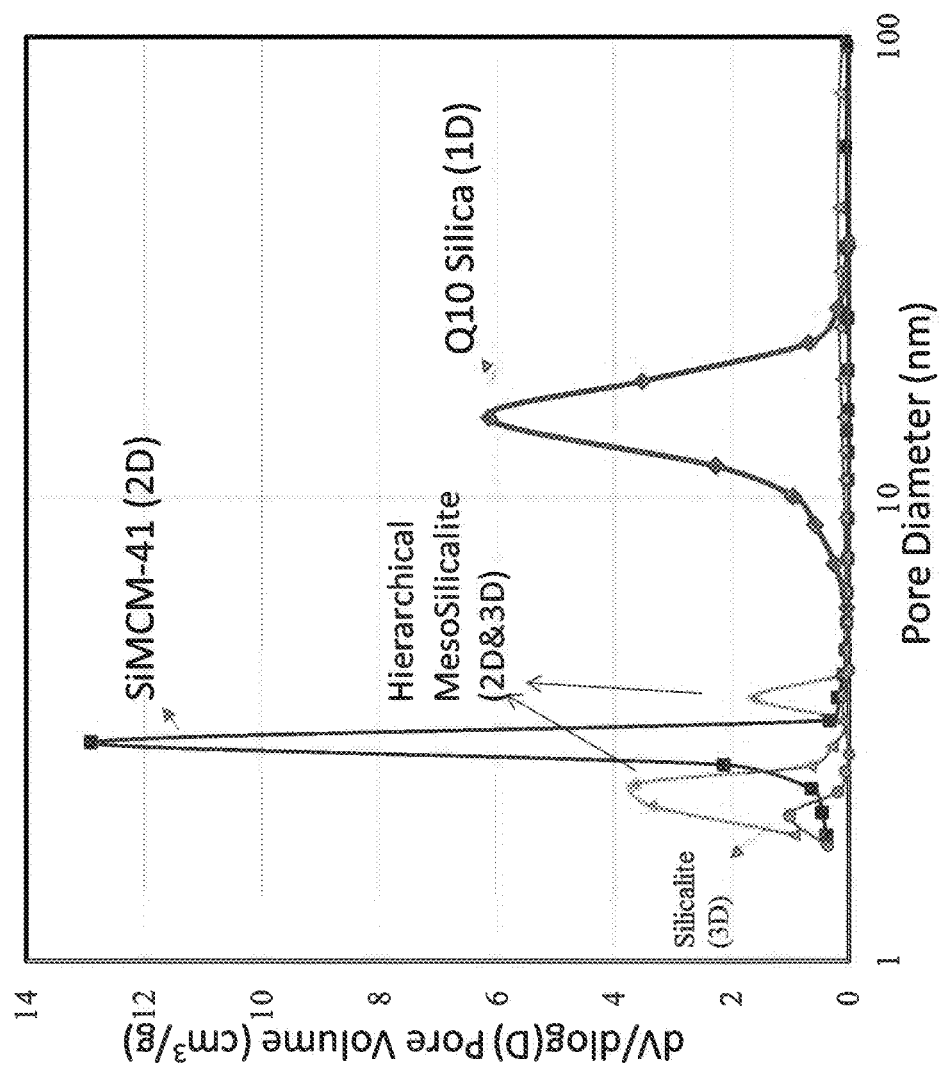
FIG. 4 is a spectrum of pore size distribution of Q10 silica, SiMCM-41, hierarchical mesosilicalite, and silicalite.
Figure 5:
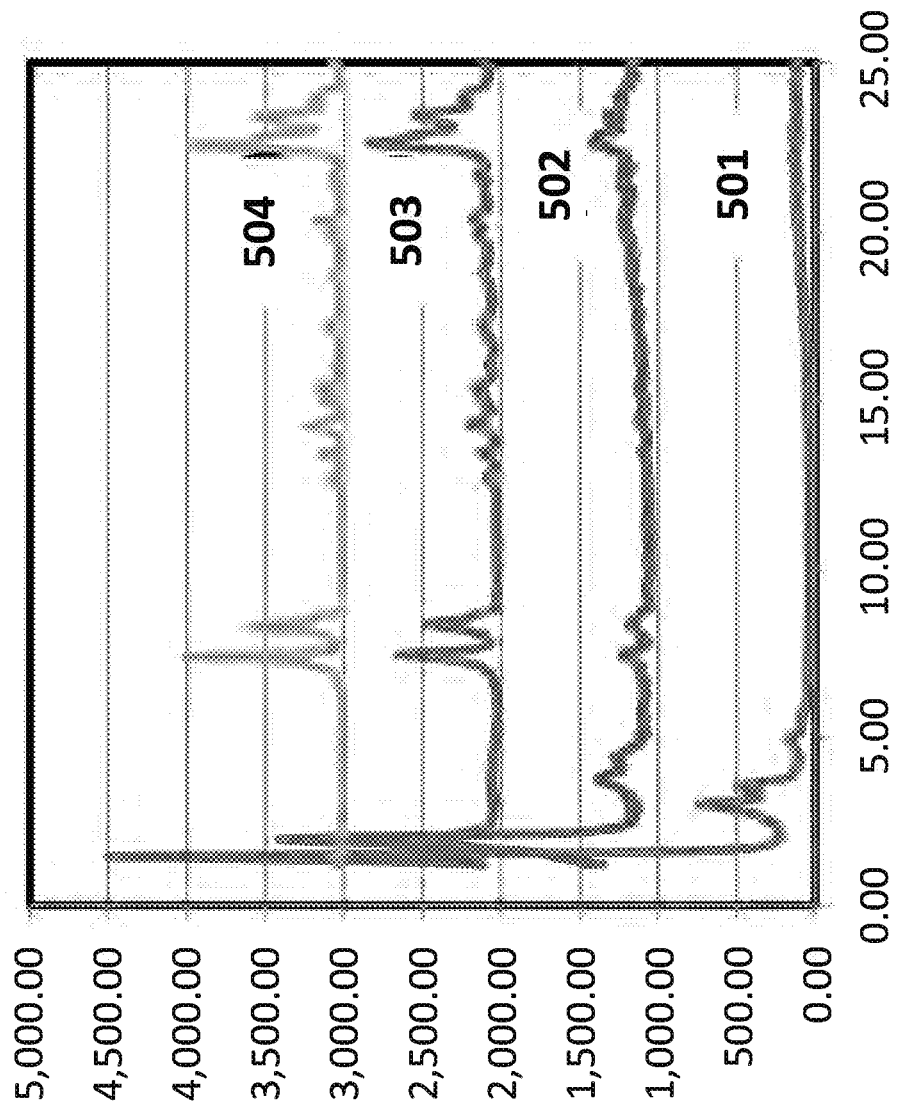
FIG. 5 is an X-Ray diffraction spectrum of hierarchical mesosilicalite, mesophase content:microphase content (70:30), mesophase content:microphase content (30:70), and parent silicalite.

Hierarchical silicalite has at least two types of pore systems with different pore size ranges, for example, a pore size range in the micropore range and a pore size range in the mesopore range. The hierarchy of the mesophase and microphase results in improved interaction with materials that can be carried, adsorbed, absorbed and/or otherwise contacted by the nanocarrier due to a greater surface area of contact with two phases instead of one phase, and an improved flow, or exchange, of the materials that may be carried into and out of the nanocarrier. FIG. 3 depicts a nitrogen adsorption isotherm of the mesosilicalite nanocarrier in comparison to SiMCM-41, Q10 silica, and a silicalite. The presence of micropores and mesopores in the nanocarrier exhibits a unique hysteresis pattern. The capillary condensation between 0.2-0.4 of the mesosilicalite nanocarrier showed the presence of micropores of the nanocarrier. The nanocarrier has a mesophase content in the range of 30% to 70%, 40% to 60%, or 40% to 50%, a microphase content in the range of 30% to 70%, 40% to 60%, or 40% to 50% relative to a total volume of the nanocarrier, and a mean pore diameter in the range of 1.5 nm to 5.5 nm, 1.75 nm to 5.25 nm, 2 nm to 5 nm, 2.5 nm to 4.5 nm, or 3 nm to 4 nm. FIG. 4 is an exemplary pore diameter distribution diagram depicting the pore diameters of the presently described nanocarrier and pores found in other nanomaterials for comparison. The pore size distribution of the nanocarrier exhibits two types of pores between 2.4 nm and 3.7 nm, while Q10 silica and SiMCM-41 each show one type of pore at 15 nm and 2.9 nm, respectively. FIG. 5 is an exemplary X-Ray diffraction spectrum of the mesosilicalite nanocarrier in comparison to other nanomaterials. The nanocarrier may comprise two types of materials, a first material having 2D properties and a second material having 3D properties. The first material may be layered under the second material, thus forming a hierarchically structured nanocarrier. The amount of mesophase and microphase was calculated based on the weight percentage of composite SiMCM-41/silicalite in comparison to parent silicalite and SiMCM-41. Alternatively, a calibration curve may be constructed from the X-Ray diffraction spectra of mesosilicalite nanocarriers synthesized from different amounts of parent silicalite and SiMCM-41. Then, the amount of mesophase and microphase may be determined from an X-Ray diffraction measurement.

In some embodiments of the mesosilicalite nanocarrier, the mesopores are in ordered structures. The ordered structure of the mesopores may be a result of a template employed in the process of preparing the mesosilicalite nanocarrier, described further herein. The template, for example a tetrapropylammonium hydroxide, may assist colloidal silica, described further in the method of preparing the mesosilicalite nanocarrier, to self-order in formation of cylindrical pores which form the hexagonal structure. The ordered structure may allow for improved diffusion of materials into and out of the nanocarrier. This characteristic may make the nanocarriers useful as drug delivery agents.

In some embodiments of the mesosilicalite nanocarrier, the nanocarrier is loaded with an antioxidant. Antioxidants may scavenge free radicals that are prevalent in prolific cancers and cause DNA damage and mutations. Antioxidants may include, but are not limited to edaravone, N-acetylcysteine, alfa-lipoic acid, diosmin, hesperidin, oxerutins, baicalein, and catechin. In some embodiments of the mesosilicalite nanocarrier the antioxidant is gallic acid. Gallic acid is a potent antioxidant against cancers (leukemia, colon and lung cancer cells) and other metabolic disorders.

In some embodiments of the mesosilicalite nanocarrier, a total recovery yield of the nanocarrier and gallic acid is in the range of 29% to 100%, 40% to 80%, or 50% to 75% at a gallic acid loading rate in the range of 0.2 mmol/g of the nanocarrier to 16 mmol/g of the nanocarrier, 0.5 mmol/g of the nanocarrier to 12 mmol/g of the nanocarrier, 1 mmol/g of the nanocarrier to 10 mmol/g of the nanocarrier, 2 mmol/g of the nanocarrier to 8 mmol/g of the nanocarrier, or 5 mmol/g of the nanocarrier to 6 mmol/g of the nanocarrier. As defined here, the total recovery yield of the nanocarrier and gallic acid is the weight percent of the recovered nanocarrier and adsorbed gallic acid, with respect to the combined weight of the initial nanocarrier and gallic acid. A total recovery yield may also be measured for other nanomaterials and other antioxidants or drugs. Preferably, the total recovery yield is determined by recovering a nanomaterial and adsorbed antioxidant after equilibrium concentrations have been reached.

Once the antioxidant is loaded into the nanocarrier, the nanocarrier may be employed in medical treatments to slowly release the antioxidant in or proximal to a tumor. For example, a surgeon may treat an inoperable tumor with the nanocarrier in an open surgical bed. A surgeon may implant the nanocarrier by a microsurgery technique or neuro-endoscopy. Upon delivering the nanocarrier to the site of treatment, the antioxidant may leave the nanocarrier. Of the total adsorbed antioxidant, 30-100 wt %, preferably 50-99 wt %, more preferably 70-99 wt %, even more preferably 80-99 wt % may diffuse out from the nanocarrier.

Figure 6:
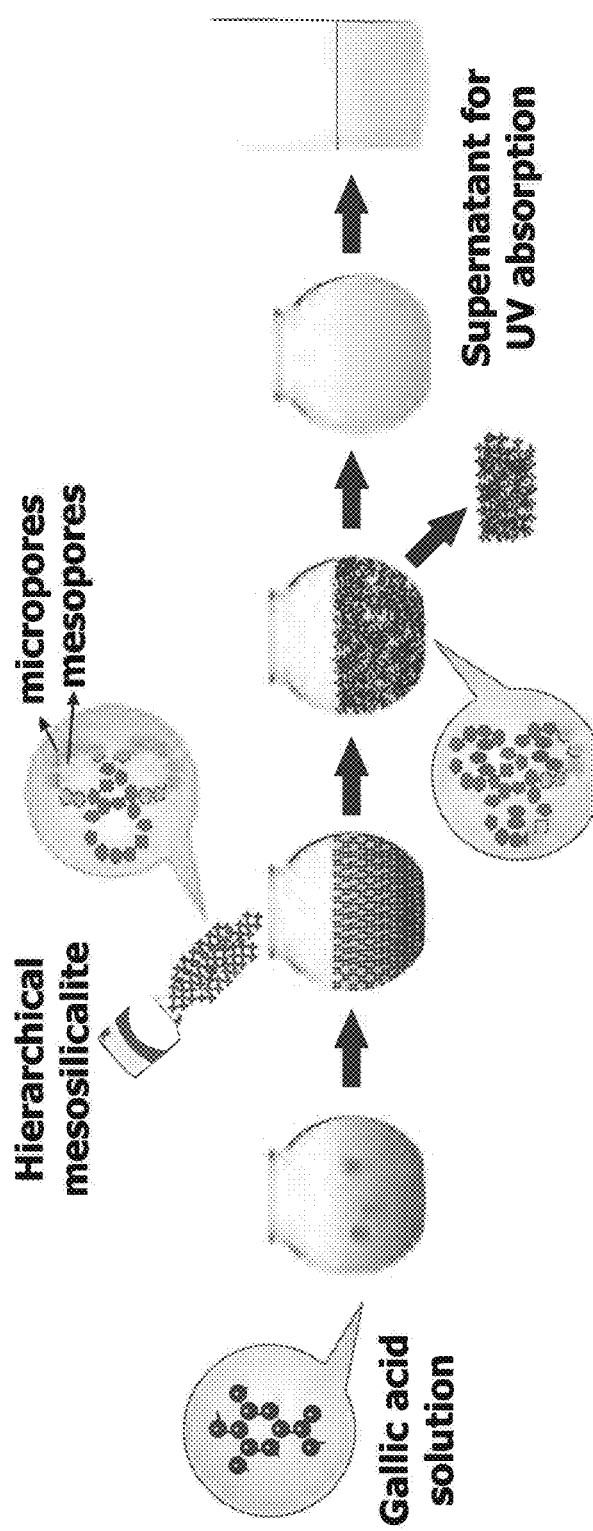
FIG. 6 is a schematic of a procedure of loading the antioxidant into the mesosilicalite nanocarrier.

According to a second aspect, the present disclosure relates to a method of loading the antioxidant into the mesosilicate nanocarrier. Loading the antioxidant includes drying the mesosilicate nanocarrier at 100° C.-120° C., 105° C.-115° C., or 110° C.-112° C. for 72 hours to 86 hours, 75 hours to 85 hours, or 78 hours to 80 hours. The dried mesosilicate nanocarrier is mixed with a solution of the antioxidant. In some implementations of the method, the solution of the antioxidant is an aqueous solution. The aqueous solution may include water, alcohol, glycerol, or a combination thereof. The purpose of drying the mesosilicate nanocarrer is to remove all traces of water to prevent pockets within the nanocarrier upon loading. In some implementations of the method, the antioxidant in the solution has a concentration of 0.25 g/L to 15 g/L, 0.5 g/L to 12 g/L, 1 g/L to 10 g/L, 2 g/L to 8 g/L, or 5 g/L to 7 g/L. The mixing of the dried mesosilicate nanocarrier with the solution of the antioxidant may continue for 12 hours to 36 hours, 15 hours to 35 hours, 18 hours to 30 hours, or 20 hours to 25 hours at a temperature of 23° C.-30° C. or 25° C.-28° C. The mixing forms the mesosilicate nanocarrier loaded with the antioxidant. In some implementations the mixing of the antioxidant in solution may be repeated by removing the mesosilicalite nanocarrier from the solution of the antioxidant and re-mixing the nanocarrier with a more concentrated solution of the antioxidant. For example, in the re-mixing, the solution may have an antioxidant concentration of 15 g/L to 25 g/L, or 18 g/L to 20 g/L. FIG. 6 depicts a cartoon schematic of a method of loading the antioxidant (gallic acid) into the mesosilicate nanocarrier. In one embodiment, the adsorbed antioxidant weight may be 10% to 50%, preferably 10% to 40% of the mesosilicate nanocarrier weight over the loading rate of 0.1 mmol antioxidant per g of the nanocarrier to 16 mmol antioxidant per g of the nanocarrier, preferably 0.3 mmol/g-16 mmol/g, more preferably 0.6-16 mmol/g. In other embodiments, the adsorbed antioxidant weight may be 4% to 12% of the mesosilicalite nanocarrier weight for similar loading rates as described, though in some embodiments, the adsorbed antioxidant weight may be higher than 50%, for example, 60%.

Figure 7:
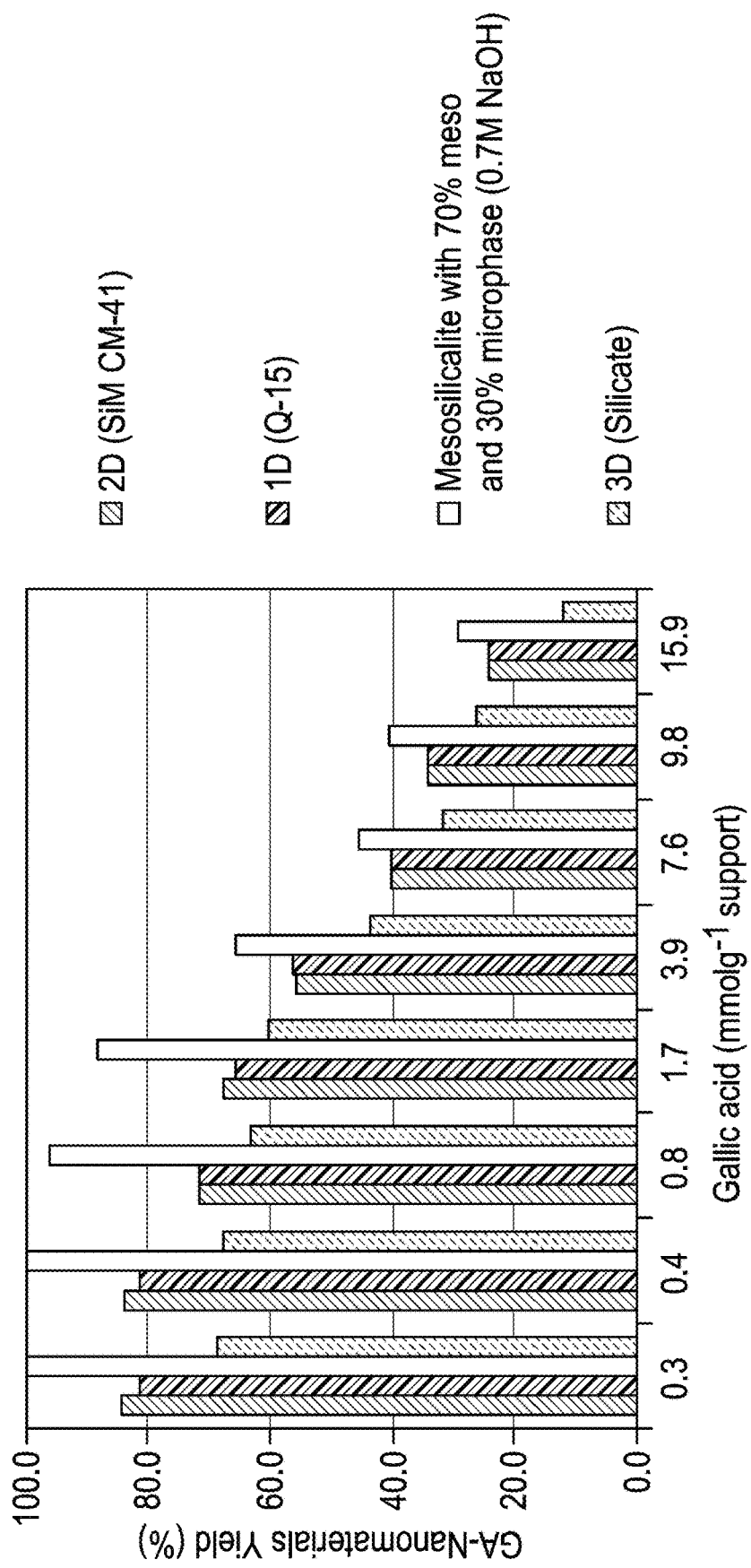
FIG. 7 is a graph of a total recovery yield of gallic acid loaded into the mesosilicalite nanocarrier.
Figure 13:
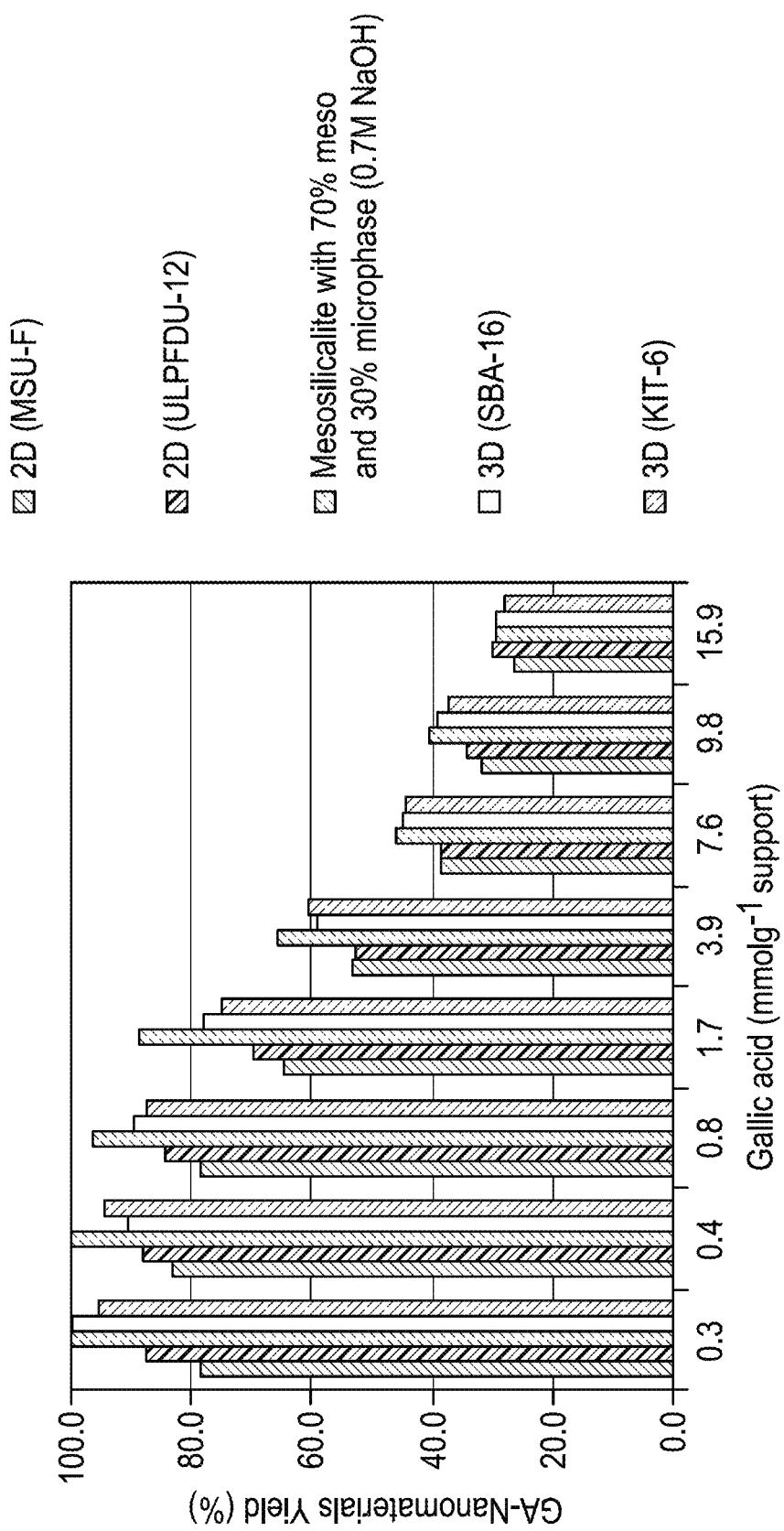
FIG. 13 is a graph of a total recovery yield of gallic acid loaded into the mesosilicalite nanocarrier having mesophase content:microphase content (70:30) compared with commercially-available mesoporous SiSBA-16, SiKIT-6, ULPFDU-12, and MSU-F.
Figure 14A:
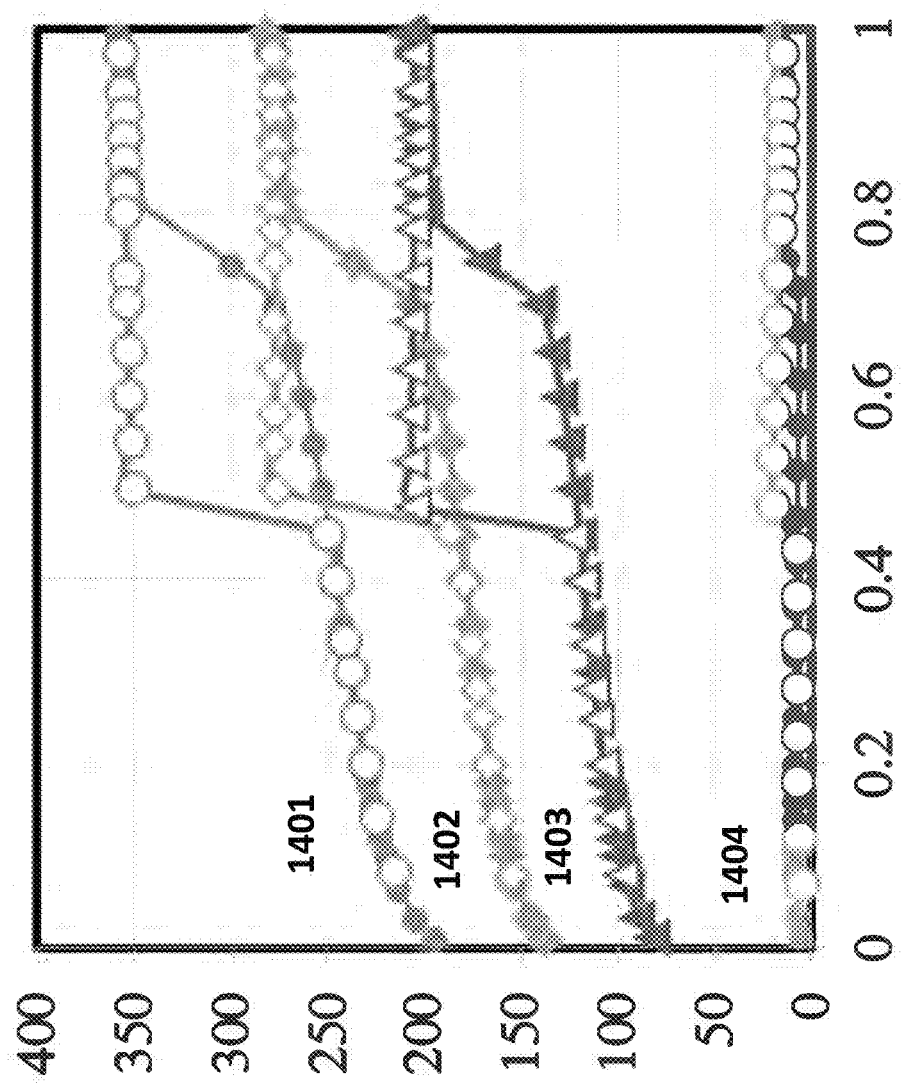
FIG. 14A is a nitrogen adsorption isotherm of the commercially-available mesoporous ULPFDU-12 nanocarrier loaded with 1.7 mmol of gallic acid/g nanocarrier, the nanocarrier loaded with 7.6 mmol of gallic acid/g nanocarrier, and the nanocarrier loaded with 15.9 mmol/g nanocarrier.
Figure 14B:
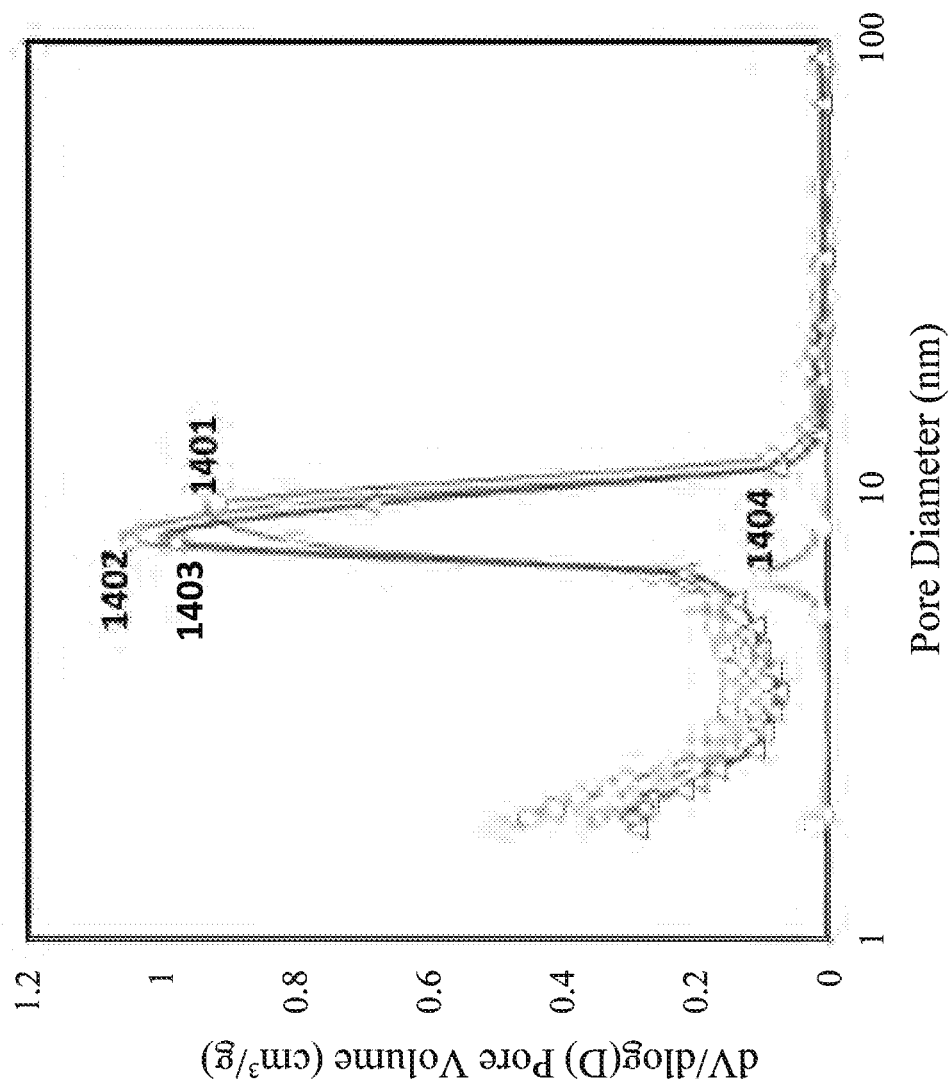
FIG. 14B is a spectrum of pore size distribution of the commercially-available mesoporous ULPFDU-12 nanocarrier, the nanocarrier loaded with 1.7 mmol of gallic acid/g nanocarrier, the nanocarrier loaded with 7.6 mmol of gallic acid/g nanocarrier, and the nanocarrier loaded with 15.9 mmol/g nanocarrier.
Figure 14C:
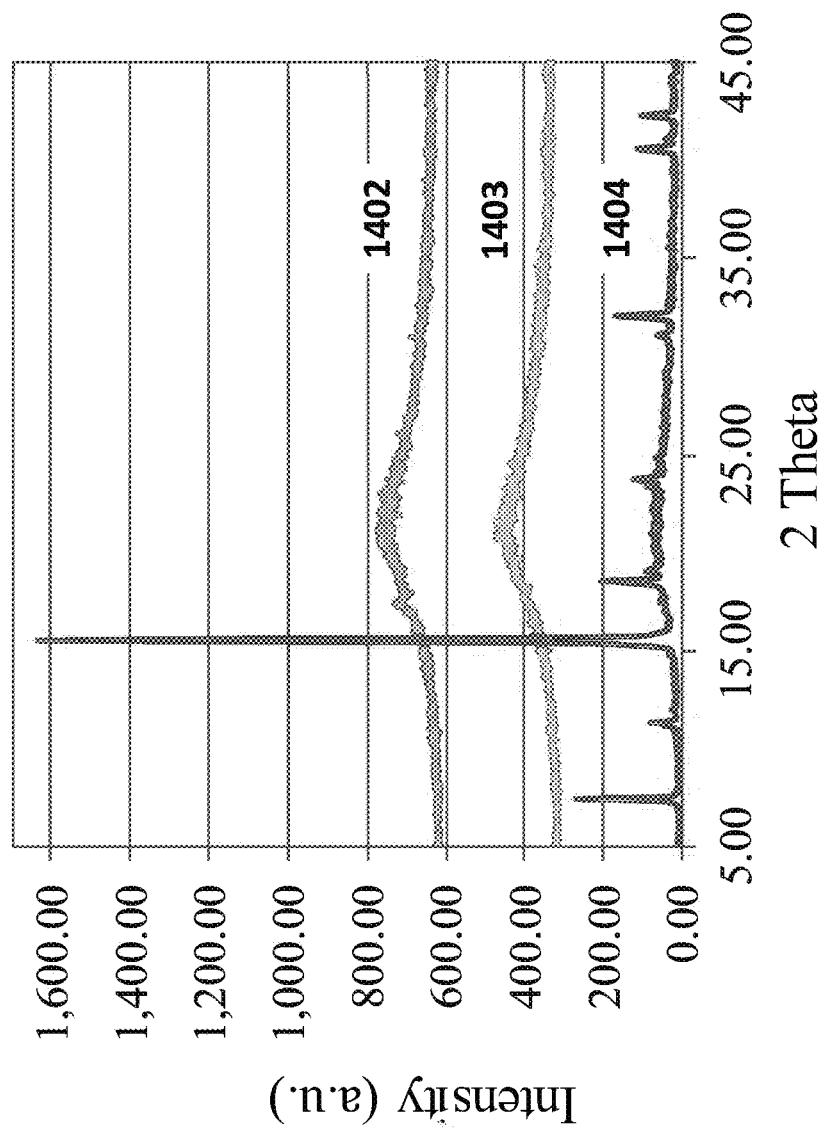
FIG. 14C is an X-Ray diffraction spectrum of the commercially-available mesoporous ULPFDU-12 nanocarrier loaded with 1.7 mmol of gallic acid/g nanocarrier, the nanocarrier loaded with 7.6 mmol of gallic acid/g nanocarrier, and the nanocarrier loaded with 15.9 mmol/g nanocarrier.
Figure 14D:
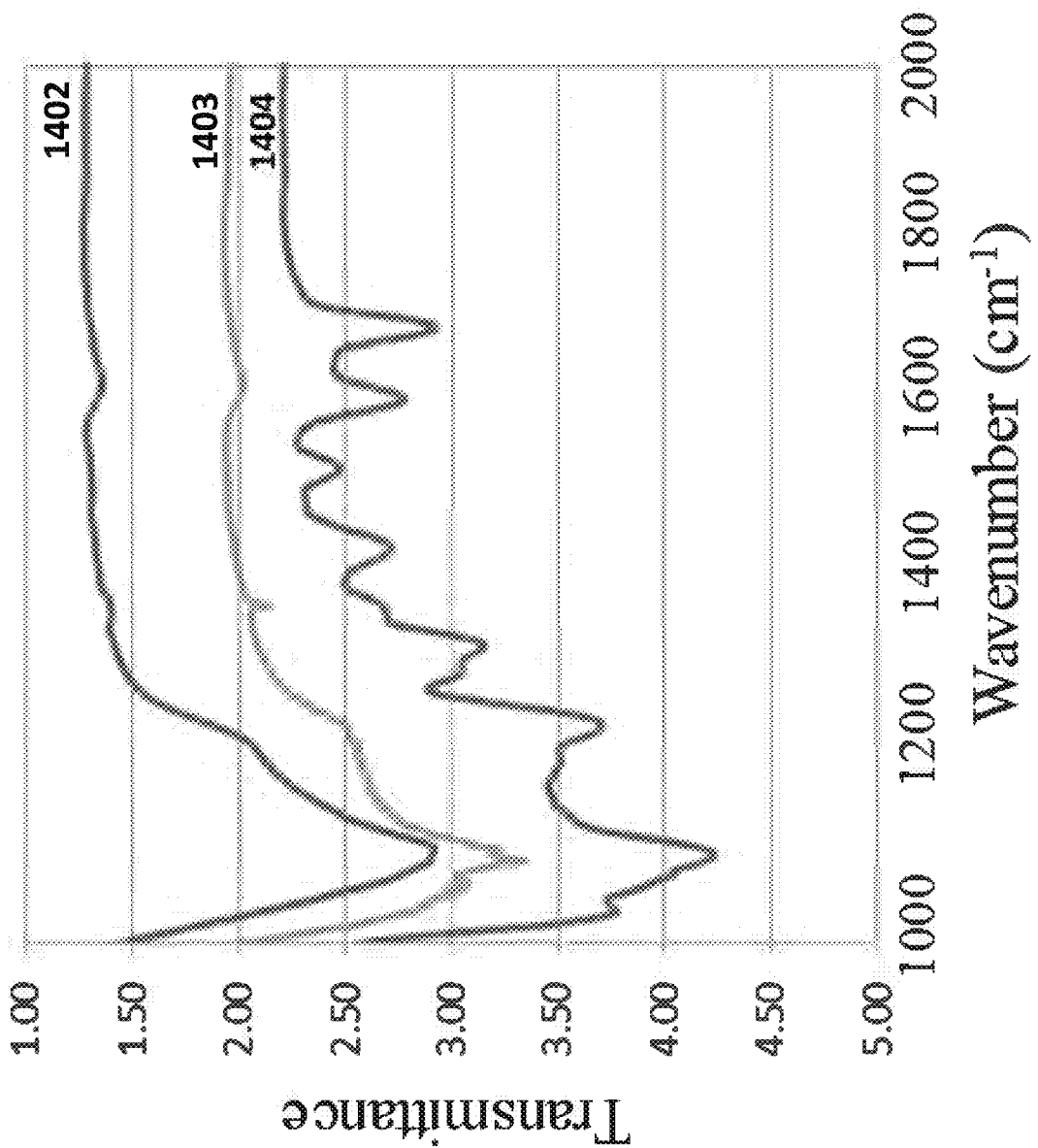
FIG. 14D is an FTIR characterization of the commercially-available mesoporous ULPFDU-12 nanocarrier loaded with 1.7 mmol of gallic acid/g nanocarrier, the nanocarrier loaded with 7.6 mmol of gallic acid/g nanocarrier, and the nanocarrier loaded with 15.9 mmol/g nanocarrier.
Figure 15A:
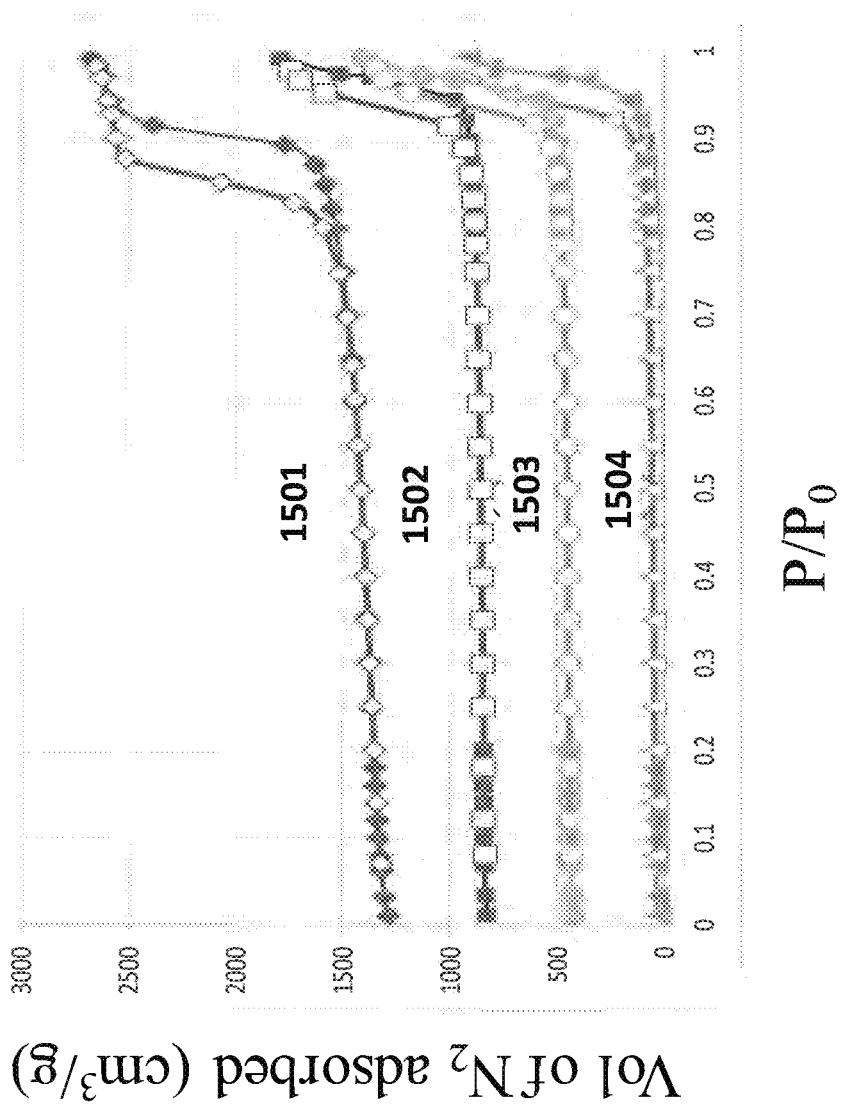
FIG. 15A is a nitrogen isotherm of external deposition of gallic acid on a commercially-available mesoporous silica cellular foam nanomaterial (MSU-F), the mesoporous silica cellular foam nanomaterial loaded with 1.7 mmol of gallic acid/g nanomaterial, the mesoporous silica cellular foam nanomaterial loaded with 7.6 mmol of gallic acid/g nanomaterial, and the mesoporous silica cellular foam nanomaterial loaded with 15.9 mmol/g nanomaterial.
Figure 15B:
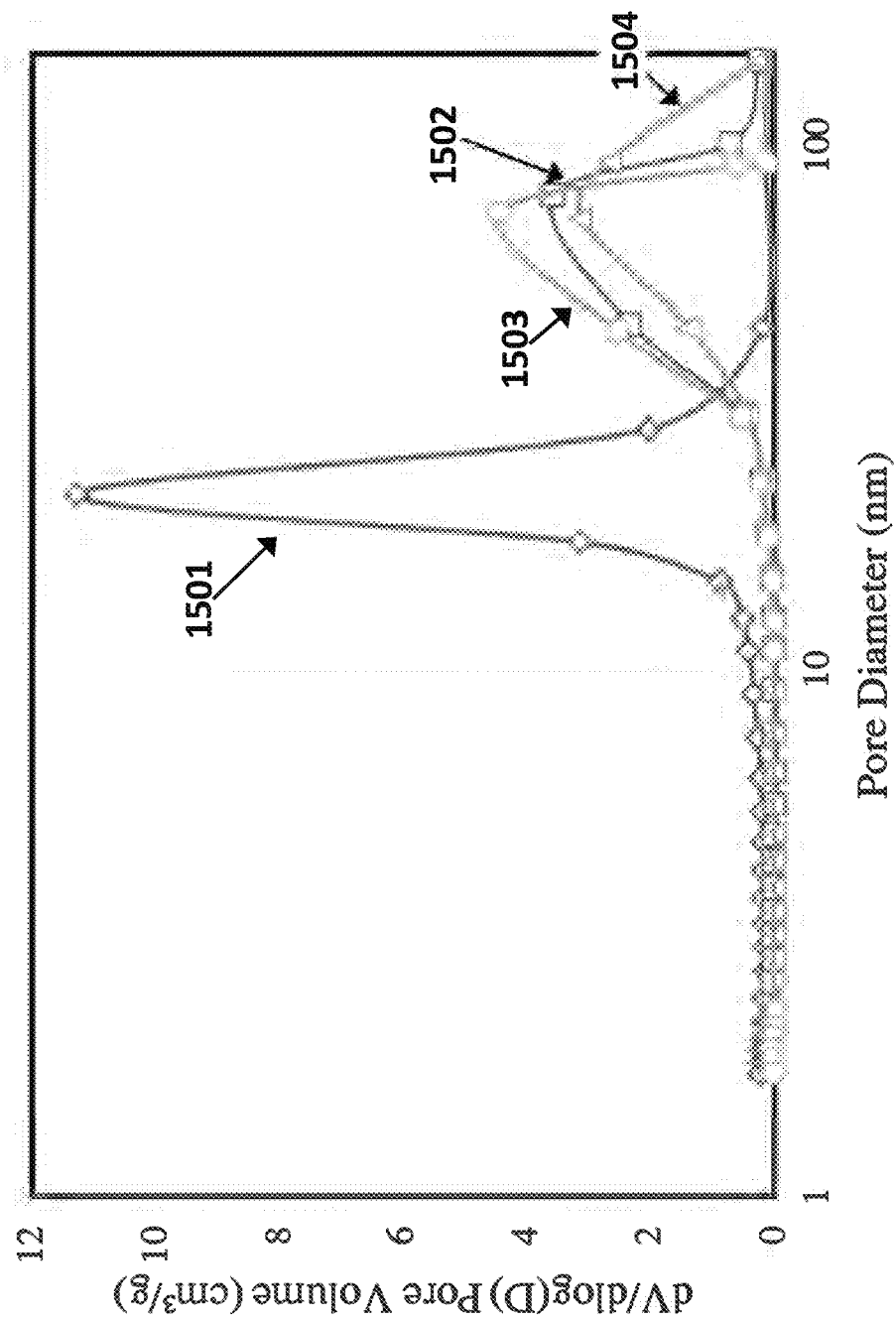
FIG. 15B is a spectrum of pore size distribution of the commercially-available mesoporous silica cellular foam nanomaterial (MSU-F), the mesoporous silica cellular foam nanomaterial loaded with 1.7 mmol of gallic acid/g nanomaterial, the mesoporous silica cellular foam nanomaterial loaded with 7.6 mmol of gallic acid/g nanomaterial, and the mesoporous silica cellular foam nanomaterial loaded with 15.9 mmol/g nanomaterial.
Figure 15C:
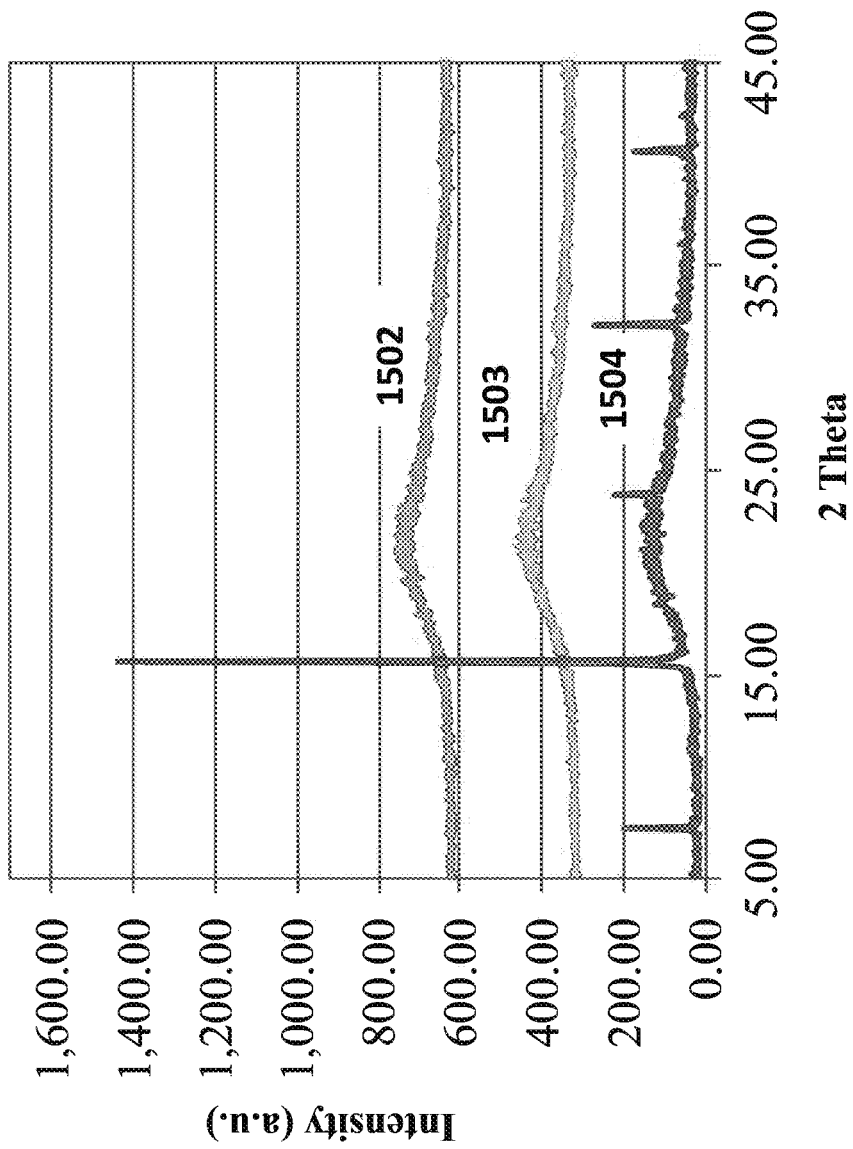
FIG. 15C is an X-Ray diffraction spectrum of commercially-available mesoporous silica cellular foam nanomaterial (MSU-F), the mesoporous silica cellular foam nanomaterial loaded with 1.7 mmol of gallic acid/g nanomaterial, the mesoporous silica cellular foam nanomaterial loaded with 7.6 mmol of gallic acid/g nanomaterial, and the mesoporous silica cellular foam nanomaterial loaded with 15.9 mmol/g nanomaterial.
Figure 15D:
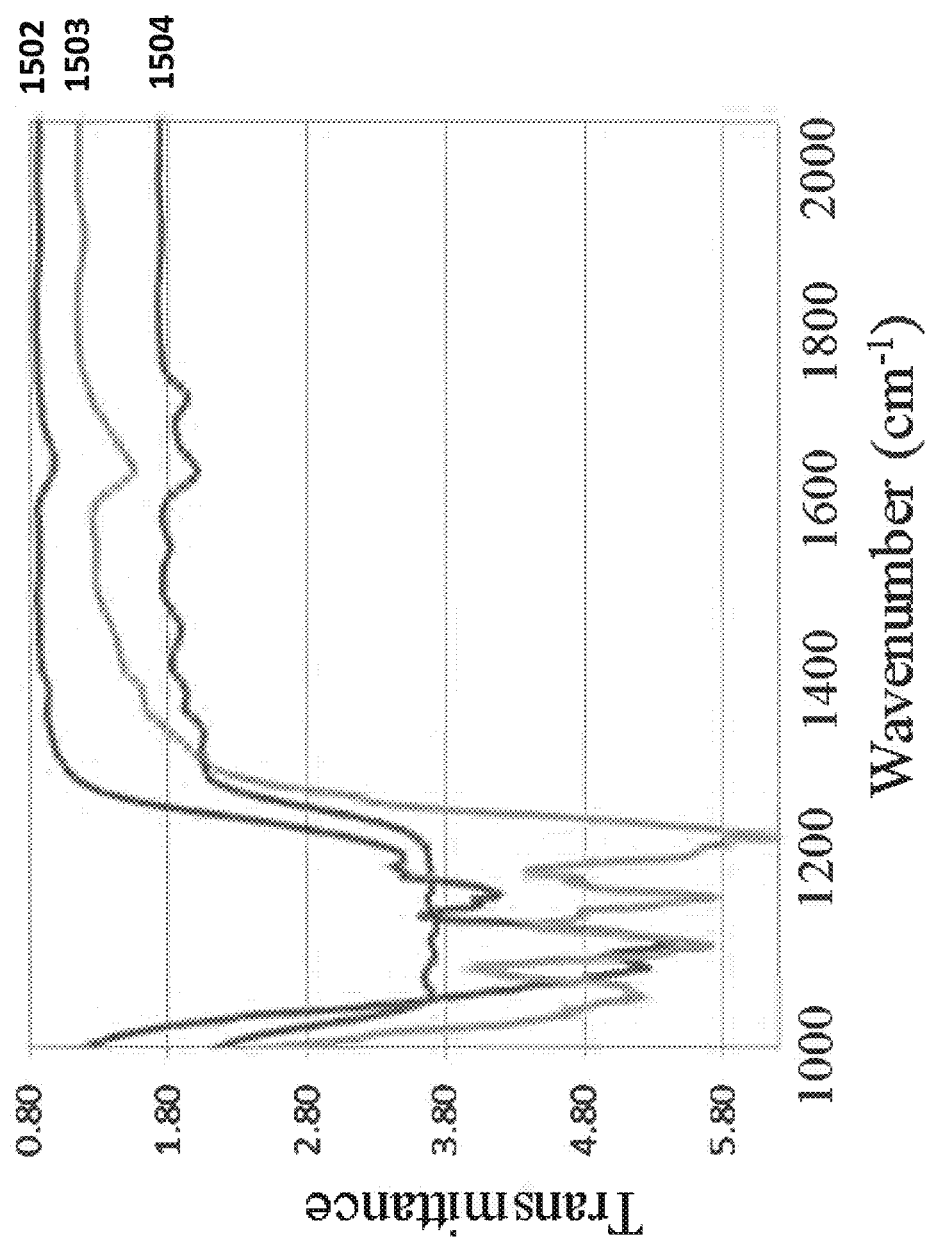
FIG. 15D is an FTIR characterization of the commercially-available mesoporous silica cellular foam nanomaterial (MSU-F), the mesoporous silica cellular foam nanomaterial loaded with 1.7 mmol of gallic acid/g nanomaterial, the mesoporous silica cellular foam nanomaterial loaded with 7.6 mmol of gallic acid/g nanomaterial, and the mesoporous silica cellular foam nanomaterial loaded with 15.9 mmol/g nanomaterial.

The method by which the antioxidant is loaded into the mesosilicalite nanocarrier is called equilibrium adsorption method. The equilibrium-adsorption method may take place in a sequence of steps in which a solution of an antioxidant solution is put into contact with the mesosilicalite nanocarrier until the solution, which may be continuously monitored, indicates no net transfer between the mesosilicalite nanocarrier and the antioxidant in solution surrounding the nanocarrier. The net transfer of the antioxidant may be measured by FTIR characterization of the antioxidant loading. FIG. 7 depicts a bar graph of the total recovery yield of the gallic acid-loaded mesosilicalite nanocarrier of the present disclosure as compared to the loading of other nanomaterials. The combination of micropores and mesopores of the presently described mesosilicalite nanocarrier exhibited higher payload capacity of antioxidant gallic acid than parent silicalite and SiMCM-41 in the following order: mesosilicalite nanocarrier>SiMCM-41>silicalite. The presently described nanocarrier has a total recovery yield of 95-100% when loaded with an antioxidant amount of 0.1 mmol/g to 1.0 mmol/g of the nanocarrier, preferably 0.2-0.9 mmol/g, more preferably 0.3-0.8 mmol/g. As FIG. 13 shows, this is a higher total recovery yield than other nanomaterials (for example SBA-16, KIT-6, ULPFDU-12, MSU-F etc.) loaded with a similar amount of antioxidant.

Figure 8:
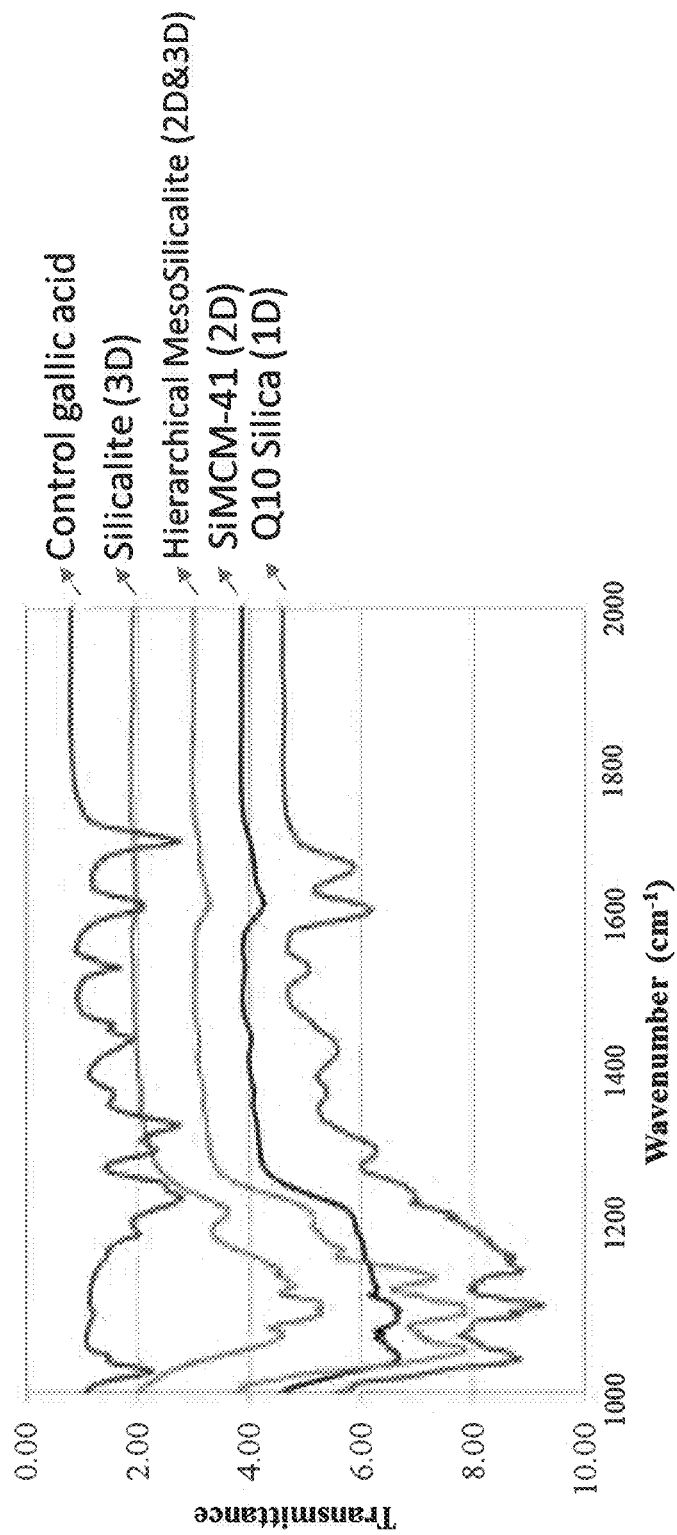
FIG. 8 is an FTIR characterization of gallic acid loading into the mesosilicalite nanocarrier, Q10 silica, SiMCM-41, silicalite and gallic acid (pure)

FIG. 8 depicts an FTIR spectrum to characterize an exemplary antioxidant, gallic acid, loaded into the nanocarrier of the present disclosure as compared to other nanomaterials. The example shows that the combination of micropores and mesopores leads to deposition of gallic acid inside the pore channels in a non-crystalline, nano-sized amorphous state, which is different than the spectrum of crystalline gallic acid without any nanocarrier present.

In some implementations, the nanosized mesosilicalites, with the mesophase and microphase interlinked (as the SiMCM-41/silicalite composite), may allow the gallic acid to convert from the crystalline form of gallic acid into an amorphous form. Conversion to an amorphous form permits adsorption of larger amounts of gallic acid inside the hierarchical pore system separately or in addition to adsorption on the external surface of the nanocarrier. In some implementations 10-50% by weight percentage of the antioxidant carried by the nanocarrier is carried in the mesopores and micropores of the nanocarrier. In other embodiments, 50% to 100%, 60% to 90% or 70% to 80% of the total antioxidant carried by the nanocarrier is carried in the mesopores and micropores.

Figure 10A:
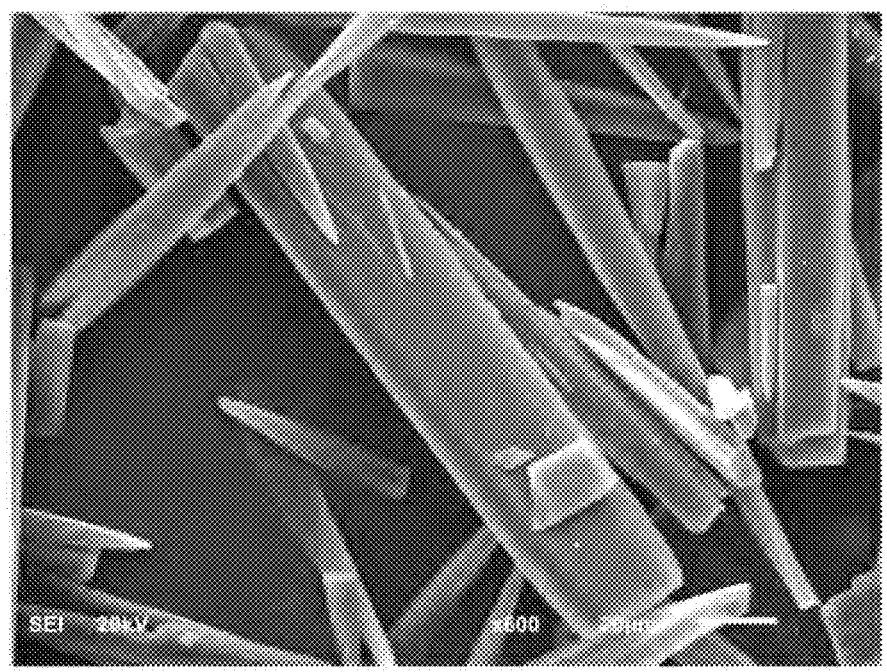
FIG. 10A is an SEM image of gallic acid.
Figure 10B:
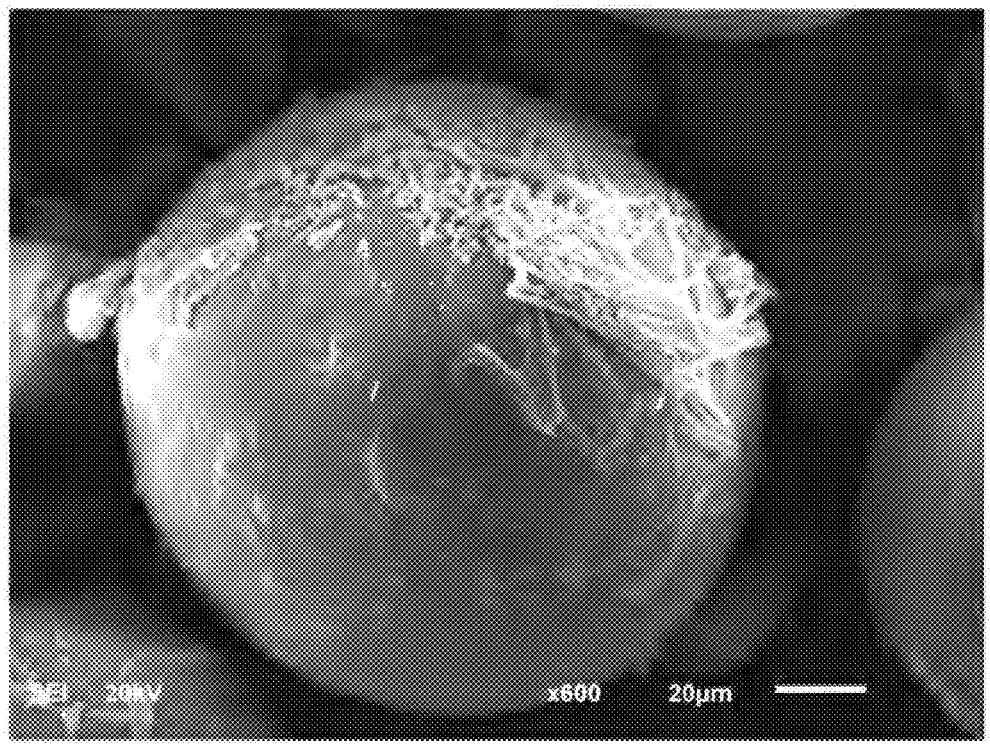
FIG. 10B is an SEM image of gallic acid loading in a Q10 silica.
Figure 11A:
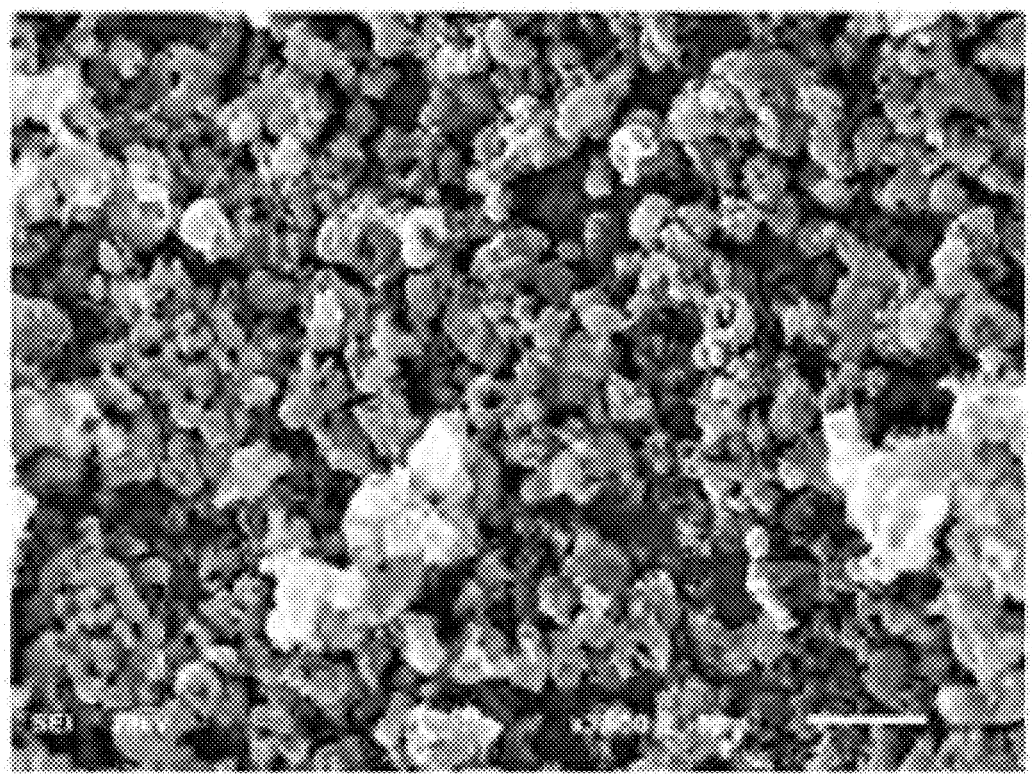
FIG. 11A is an SEM image at 3000× of gallic acid loading in the mesosilicalite nanocarrier.
Figure 11B:
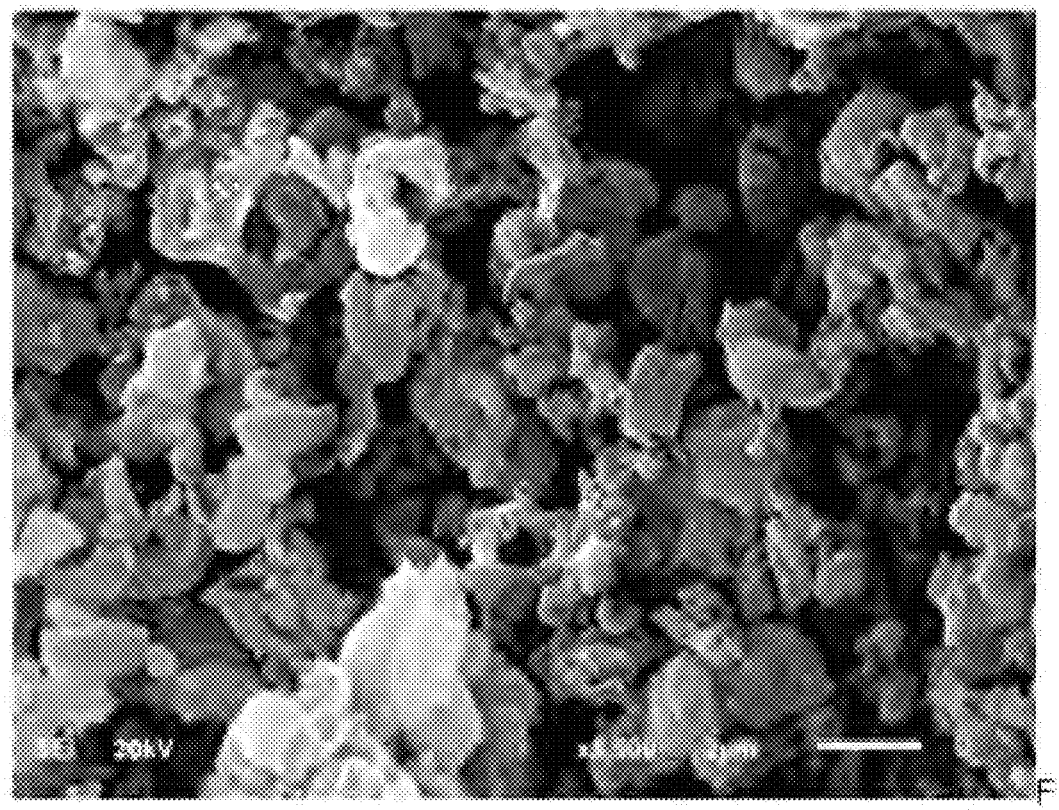
FIG. 11B is an SEM image at 6500× of gallic acid loading in the mesosilicalite nanocarrier.
Figure 12A:
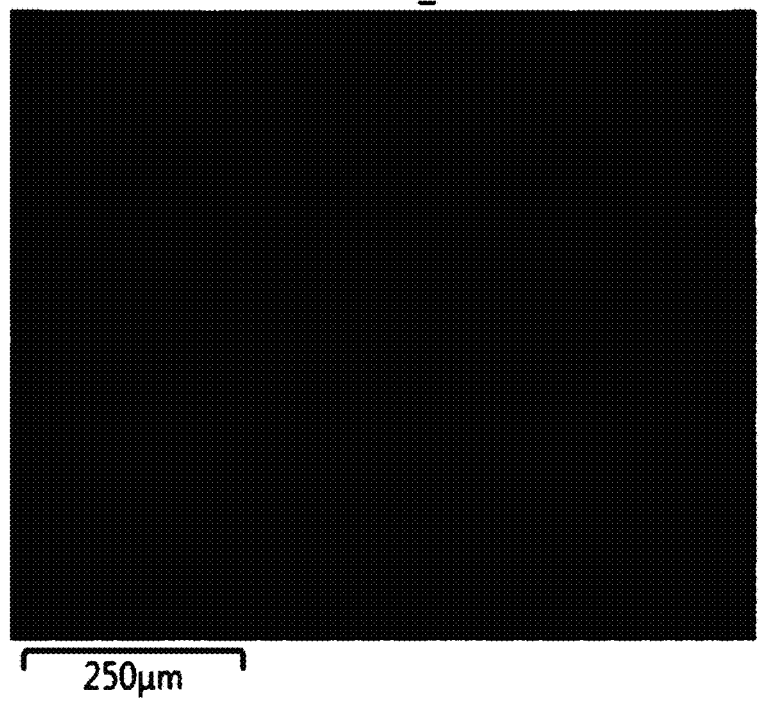
FIG. 12A is an SEM-EDX pattern of gallic acid dispersion in Q10 silica.
Figure 12B:
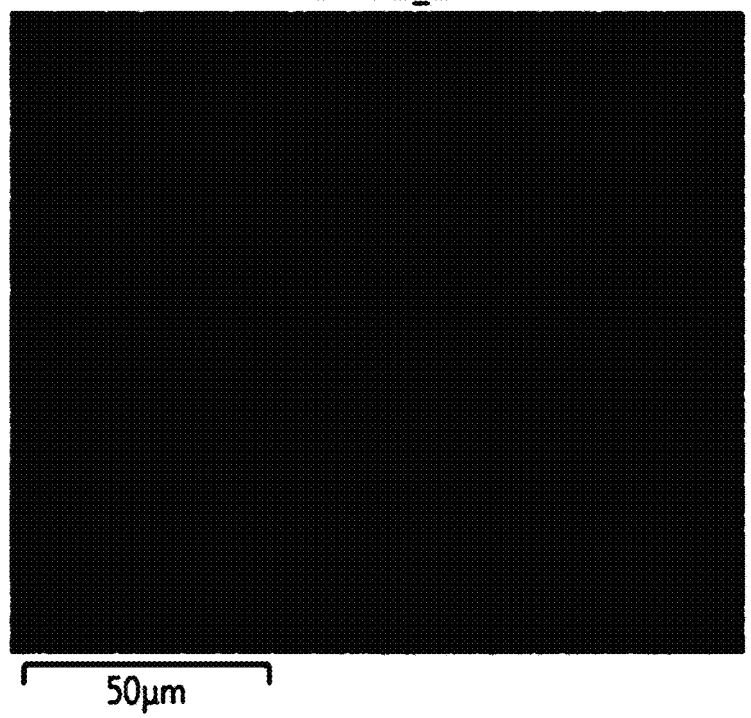
FIG. 12B is an SEM-EDX pattern of gallic acid dispersion in the mesosilicalite nanocarrier.

FIG. 10A depicts an SEM image of gallic acid and FIG. 10B depicts an SEM image of silica having gallic acid deposited over the surface of the silica. FIG. 10A and FIG. 10B indicate that the gallic acid in a crystalline state is adsorbed on the external surface of silica colloid. FIG. 11A and FIG. 11B depict the mesosilicalite nanocarrier loaded with gallic acid. FIG. 11A and FIG. 11B do not exhibit gallic acid on the surface of the nanocarrier in crystalline form. FIG. 11A and FIG. 11B indicate that nano-sized gallic acid is adsorbed into the mesopores and micropores of the mesosilicalite nanocarrier. FIG. 12A and FIG. 12B compare an SEM of an energy dispersive X-ray pattern of gallic acid in silica and gallic acid in mesosilicalite, respectively. The pattern shows a greater number of dispersive bright regions ("dots") representative of the uniform deposition of gallic acid in mesosilicalite nanocarrier as compared to Q10 silica.

According to a third aspect, the present disclosure relates to a method of preparing the mesosilicalite nanocarrier including mixing a silica source with a template to form a first mixture. The first mixture is then hydrothermally aged at a temperature of 150° C.-200° C. or 155° C.-175° C. for 24 hours to 86 hours, 36 hours to 72 hours, 48 hours to 60 hours. In some implementations, the first mixture is filtered. The filtering may be accomplished by a surface filter, in which a solid sieve traps the solid particles of the first mixture, with or without the aid of filter paper. The filtering may employ a Büchner funnel, belt filter, rotary vacuum-drum filter, cross-flow filters, or a screen filter. In some implementations, after filtering, the retrieved solids of the first mixture are washed by water or an alcohol and water mixture, and then the solids of the first mixture are dried to form a silicalite. Next, treating the silicalite with an alkaline solution and a surfactant forms a second mixture. The second mixture is hydrothermally aged at a temperature of 60° C.-120° C., 70° C.-110° C., or 80° C.-100° C. for 12 hours to 36 hours, 18 hours to 30 hours, or 22 hours to 25 hours at a rate of 3° C./min to 6° C./min, or 4° C./min to 5° C./min. The hydrothermal aging of the second mixture is followed by neutralizing a pH of the hydrothermally aged second mixture to a pH between 6.5 and 7.5, or 6.8 and 7.2, and a second hydrothermal aging of the aged second mixture at a temperature of 60° C.-120° C., 70° C.-110° C., or 80° C.-100° C. for 12 hour to 36 hours, 18 hours to 30 hours, or 22 hours to 25 hours at a rate of 3° C./min to 6° C./min, or 4° C./min to 5° C./min. The second hydrothermal aging may optionally be followed by filtering, washing, and drying, in a manner described above for the first mixture, to form the mesosilicalite nanocarrier. The drying steps are included due to a potential for water to create air pockets in the nanocarrier, thus thorough drying may be important for loading a maximum amount of drug or antioxidant in the carrier.

In some implementations of the method, the silica source is colloidal silica. Colloidal silicas are suspensions of fine amorphous, nonporous, and typically spherical silica particles in a liquid phase. In some implementations of the method, the colloidal silica has a surface area in the range of 120 $m^2/g$ to 150 $m^2/g$, 130 $m^2/g$ to 140 $m^2/g$, or 132 $m^2/g$ to 135 $m^2/g$. In some implementations of the method, the colloidal silica has a density in the range of 1.15 g/mL to 1.35 g/mL, or 1.2 g/mL, to 1.3 g/mL at 20° C.-30° C.

The silicalite prepared by the above described method, in some implementations, is a crystal having a crystal size of 1 µm to 5 µm, 1.5 µm to 4.5 µm, 2 µm to 4 µm, or 2.5 µm to 3.5 µm.

In some implementations, the method further includes calcining the silicalite after the drying step, wherein the calcining takes place at a temperature in the range of 545° C.-605° C., 555° C.-595° C., 565° C.-585° C., 570° C.-580° C. for 5 hours to 11 hours, 6 hours to 10 hours, or 7 hours to 9 hours and at a rate of 3° C./min to 6° C./min, or 4° C./min to 5° C./min. In some implementations, the method further includes calcining the mesosilicalite nanocarrier in a temperature range 545° C.-605° C., 555° C.-595° C., 565° C.-585° C., or 570° C.-580° C. after the drying step. This calcining may go on for a duration of 5 hours to 11 hours, 6 hours to 10 hours, or 7 hours to 9 hours and at a rate of 3° C./min to 6° C./min, or 4° C./min to 5° C./min. Either calcining step may be carried out under air, nitrogen, argon or a combination thereof. The mixture of gas may be 60% to 100%, or 70% to 90% nitrogen and 0% to 80%, 10% to 70%, or 30% to 50% argon.

In preparing the nanocarrier the template is employed to provide an initial structure to nucleate the crystal growth. The template may be referred to as a structure directing agent and is stable under hydrothermal aging conditions and furthermore hydrophobic relative to silica. Templates form structures in solution that have comparable micropore size of the intended silicalite. In some implementations of the method, the template is tetrapropylammonium hydroxide, tetraethylammonium hydroxide, tetrabutylammonium hydroxide, or tetrapentylammonium hydroxide. Commonly during calcining at temperatures that exceed 545° C., the template decomposes.

In preparing the mesophase of the nanocarrier, the surfactant may act as a nucleation site. In some implementations of the method, the surfactant is at least one of an alkylammonium halide or alkylammonium hydroxide. In some implementations of the method, the surfactant may be cetyl trimethylammonium bromide, cetyl triethylammonium bromide, or dodecyl triethylammonium bromide, Pluronic F127, Pluronic P123, Brij-56, or Brij-30 as mentioned herein.

Figure 9:
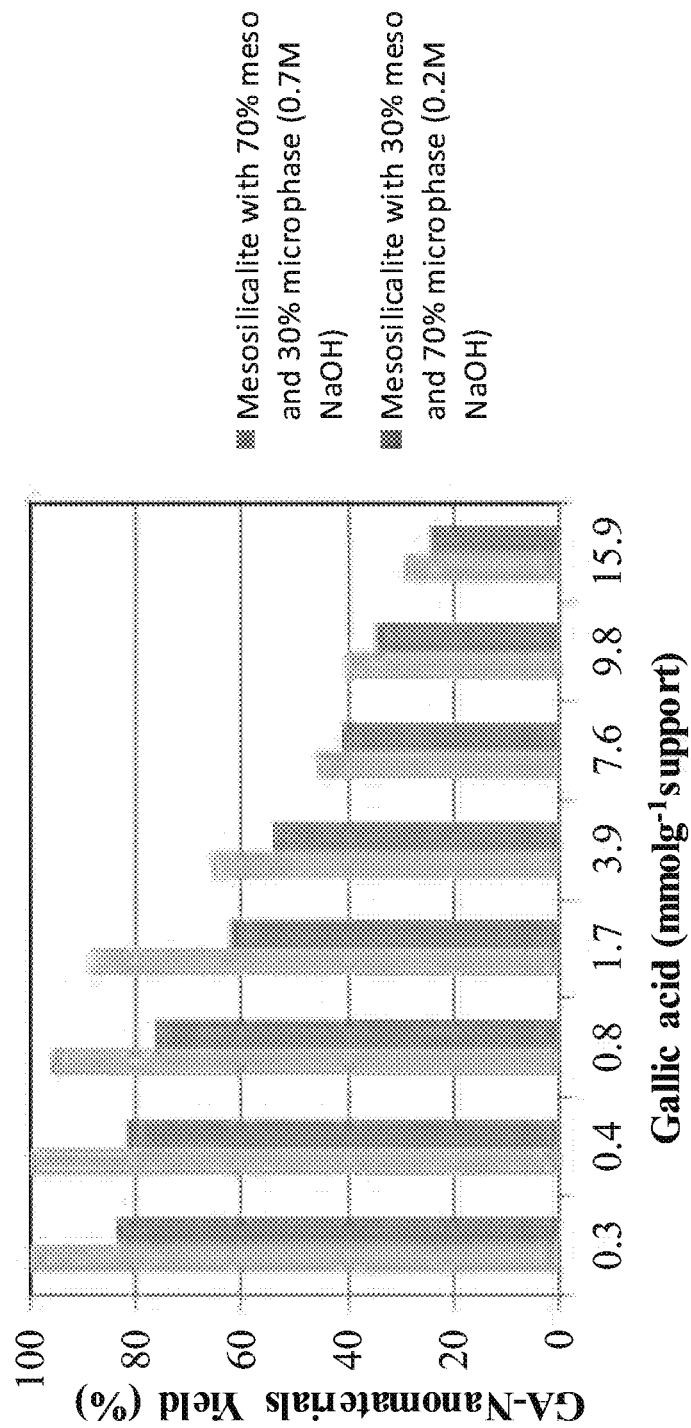
FIG. 9 is a graph depicting a variation of the total recovery yield of gallic acid loaded into the mesosilicalite nanocarrier with different weight percentages of meso and micropores.

In some implementations of the method, the alkaline solution comprises a base selected from the group consisting of sodium hydroxide, potassium hydroxide, lithium hydroxide, and barium hydroxide in a concentration range of 0.1 M to 0.8 M, 0.2 M to 0.7 M, 0.3 M to 0.6 M, or 0.4 M to 0.5 M. In some implementations a pore size may be adjusted by adjusting the concentration of the base in the alkaline solution. FIG. 9 depicts a graph of the total recovery yield that is different in mesosilicalite nanocarrier having a mesophase content (70%) and microphase (30%) employing 0.6 M NaOH to 0.8 M NaOH solution as compared to the total recovery yield of a mesosilicalite nanocarrier having a mesophase content (30%) and microphase (70%) content employing 0.2 M NaOH to 0.8 M NaOH solution.

In some implementations of the method, the alkaline solution consists of sodium hydroxide in water at a concentration of 0.2 M to 0.7 M, 0.3 M to 0.6 M, or 0.4 M to 0.5 M.

In some implementations, the nanocarrier may be adjusted to accommodate cancer therapeutics such as, but not limited to trastuzumab, vemurafenib, and imatinib mesylate. In some implementations the nanocarrier loaded with an antioxidant may be employed in treatment of cancer in combination with other cancer therapeutic regimens such as antibody drug conjugates, hormone therapies, chemotherapy, immunotherapy, and radiation therapy.

The examples below are intended to further illustrate the mesosilicalite nanocarrier, the loading of the mesosilicate nanocarrier with gallic acid, and the preparation of the mesosilicate nanocarrier and are not intended to limit the scope of the claims.

EXAMPLE 1

An engineered silicalite (mesosilicalite) was developed as a nanocarrier for antioxidant adsorption and drug delivery application. The method describes the preparation of silicalite by (a) adding silica source, (b) adding surfactant, (c) hydrothermal treatment with stirring at 60 rpm, (d) filteration, washing, and drying. FIG. 1 represents the schematic procedure for silicalite (3D) preparation and conversion of silicalite into hierarchical siliceous mesosilicalite (2D & 3D) using top-down approach.

The micropore surfactant was an alkylammonium hydroxide or halide group. The silicalite may be further calcined to remove the template at high temperatures. The calcination was carried out in the presence of air or nitrogen. The temperatures for calcination were about 550-600° C. for 6-10 h.

The silica to aluminium molar ratio of silicalite was greater than 1000 and between 1000-3000. The nanocarrier utilizes silicalite, as the source for hierarchial mesosilicalite synthesis through top-down approach methodology. The method exhibits the development of hierarchical mesosilicalite having hexagonal mesopores similar to that of siliceous MCM-41 composite. The hexagonal mesopores exhibited ordered and disordered forms.

The mesosilicate nanocarrier includes a silicalite phase (3D) and a hexagonal siliceous mesoporous phase (2D) that can be adjusted depending on the alkaline solution molarity (between 0.2-0.7 M NaOH solution). FIG. 2 depicts the X-ray diffraction of one dimensional Q10 silica, two dimensional siliceous MCM-41, three-dimensional silicalite, and developed hierarchical siliceous mesosilicalite in calcined forms. The XRD pattern shows the combination of siliceous hexagonal mesoporus form (at low angle of 2 theta) and silicalite form (at high angle of 2 theta). FIG. 3 shows the nitrogen adsorption isotherm of one-dimensional Q10 silica, two-dimensional siliceous MCM-41, three-dimensional silicalite, and developed hierarchical siliceous mesosilicalite in calcined forms. The presence of micropores and mesopores in siliceous composite is clearly shown with a unique hysteresis pattern. The capillary condensation ($P/P_0$) between 0.2-0.4 of that composite showed the presence of micropores of silicalite.

Further, the preparation of mesosilicalite is described in FIG. 1 by (a) adding mesoporous template in presence of base with mild heating for template dissolution, (b) adding silicalite to the medium, (c) dissolution of silicalite at 95° C. in stagnant position (without stirring) in oven, (d) pH adjustment, and (e) hydrothermal treatment at 95° C. in stagnant position (without stirring), (g) filteration, washing, and drying. The dissolution of silicalite phase occurs through hydrothermal heating in stagnant condition. The mesosilicalite can be further calcined to remove the template at high temperatures. The calcination was carried out in the presence of air or nitrogen. The temperature for calcination was about 550° C.-600° C. for 6-10 h. The pores may be tuned and adjusted depending on the molecular size of antioxidant and drugs. FIG. 4 shows the pore size distribution of one-dimensional Q10 silica, two-dimensional siliceous MCM-41, three-dimensional silicalite, and developed hierarchical siliceous mesosilicalite in calcined forms. The pore size distribution of hierarchical silicalite/MCM-41 shows the generation of two types of pores between 2.4 nm and 3.7 nm, while one dimensional Q10 silica and two-dimensional 2D SiMCM-41 shows one type of pores at 15 nm and 2.9 nm, respectively. FIG. 5 shows developed hierarchical mesosilicalite with tunable meso and microphase contents: parent SiMCM-41 501, mesophase content (70%) and microphase content (30%) using 0.7M NaOH solution 502, mesophase content (30%) and microphase content (70%) using 0.2M NaOH solution 503, and parent silicalite 504.

The crystal size of silicalite used for hierarchical mesosilicalite is about 1-2 μm. Such hierarchical mesosilicate may be most suitable for antioxidant gallic acid adsorption through equilibrium adsorption technique. 0.25 to 15 g/L of gallic acid solution was prepared in water for loading. The antioxidant adsorption study includes (a) drying hierarchical nanoparticles at 110° C. for 78 h, (b) addition of 0.1 g of nanoparticle in Teflon beaker filled with 20 g of stock solution (pH ~3) and (c) equilibrium adsorption through stirring (300 rpm) for 24 h at room temperature. FIG. 6 represents the schematic procedure for equilibrium adsorption of gallic acid by hierarchical siliceous mesosilicalite of present invention.

The developed hierarchical mesosilicalite has a higher payload capacity of antioxidant gallic acid compared to parent silicalite with typical micropores, and compared to parent SiMCM-41 with typical mesopores. The developed hierarchical mesosilicalite has a higher payload capacity compared to other commercially-available mesoporous silicas such as SBA-16, KIT-6, ULPFDU-12, and MSU (cellular foam). Improved payload of antioxidant is primarily attributed to a presence of nanosized hierarchical micro/mesopore channels interlinked with silicalite and hexagonal mesophase. The nanocarrier was able to convert gallic acid into an amorphous form in the nanosize range and able to incorporate greater amounts inside the pore volume. The presence of nanosized gallic acid inside the designed pores indicates that the developed nanocarrier may stop the burst release, which plagues other nanocarriers, and may improve the targeted therapeutic utility of the presently described mesosilicalite nanocarrier. The presently disclosed method simplifies the production of mesosilicalite nanocarriers, is reproducible, and is scalable based on pharma industry requirements.

FIG. 7 shows the total recovery yield (GA-Nanomaterials Yield) of gallic acid loading by hierarchical siliceous mesosilicalite of the present invention and a comparison of loading over one-dimensional Q10 silica, conventional parent siliceous MCM-41, and three-dimensional silicalite. The combination of micropores of silicalite and siliceous hexagonal mesopores of MCM-41 type showed higher payload capacity of antioxidant gallic acid than parent silicalite and SiMCM-41 in the following order: mesosilicalite>SiMCM-41>silicalite. Mesosilicalite is the nanocarrier of the present disclosure.

FIG. 8 shows FTIR characterization of gallic acid loading (15.9 mmol of gallic/g of nanomaterial) by hierarchical siliceous mesosilicalite of present invention and comparative loading over one-dimensional Q10 silica, conventional parent siliceous MCM-41, and three-dimensional silicalite. The example shows that the combination of micropores and mesopores leads to deposition of gallic acid in the pore channels in an amorphous state rather than crystalline deposition of gallic acid at the external surface similar to control gallic acid.

FIG. 9 shows the variation of total recovery yield of gallic acid (GA-Nanomaterials Yield) loading by hierarchical siliceous mesosilicalite with (a) mesophase content (70%) and microphase (30%) using 0.7M NaOH solution and (b) mesophase content (30%) and microphase (70%) content using 0.2M NaOH solution.

FIG. 10A and FIG. 10B show SEM images of gallic acid loading (15.9 mmol of gallic/g of nanomaterial) by one-dimensional Q10 silica at same scale of 20 μm. The example shows the presence of gallic acid on the external surface of Q10 silica but not inside the pores. The presence of crystalline deposition of gallic acid similar to control gallic acid is clearly shown.

FIG. 11A and FIG. 11B show SEM images of gallic acid loading (15.9 mmol of gallic/g of nanocarrier) by hierarchical siliceous mesosilicalite of present invention at 5 μm and 2 μm scales, respectively. The example shows the absence of crystalline gallic acid on the external surface of mesosilicalite. The presence of silicalite (2 μm) in the composite is clearly shown.

FIG. 12A and FIG. 12B show SEM-Energy Dispersive X-ray (EDX) patterns of gallic acid dispersion at 15.9 mmol of gallic loading per g of nanomaterial by Q10 silica (FIG. 12A) and hierarchical siliceous mesosilicalite of present invention (FIG. 12B). The example shows the uniform deposition of gallic acid in hierarchical siliceous mesosilicalite compared to Q10 silica.

FIG. 13 shows the total recovery yield of gallic acid loaded nanomaterials of different structures over different mmol of gallic acid loading per gram of nanomaterial through equilibrium adsorption technique. The hierarchical siliceous mesosilicalite of present invention showed high payload ability and stability in acidic loading medium in the following order: mesosilicalite>SiSBA-16>SiKIT-6>ULPFDU-12>MSU-F.

FIG. 14A-FIG. 14D shows the example of negative result of Ultralarge pore FDU-12 nanomaterial at high gallic acid loading. Support alone 1401, 1.7 mmol of gallic acid/g nanomaterial 1402, 7.6 mmol of gallic acid/g nanomaterial 1403, and 15.9 mmol of gallic acid/g of nanomaterial 1404. The result shows the existence of crystalline form of gallic acid at the external surface with loading of 15.9 mmol of gallic acid/g of nanomaterial. Such external dispersion of antioxidants will lead to burst release, and are proposed to be not suited as drug carrier.

FIG. 15A-FIG. 15D shows the example of external deposition of crystalline gallic acid on mesoporous silica cellular foam nanomaterial at high gallic acid loading. Support alone 1501, 1.7 mmol of gallic acid/g of nanomaterial 1502, 7.6 mmol of gallic acid/g nanomaterial 1503, and 15.9 mmol of gallic acid/g of nanomaterial 1504. The result shows the existence of crystalline form of gallic acid at high loading at the external surface. Such external dispersion of antioxidants will lead to burst release, and are proposed to be not suitable for drug carrier involving antioxidant gallic acid.

A hierarchical mesosilicalite nanocarrier with mesopores and micropores has been provided in the above example. This hierarchical mesosilicalite nanocarrier may be employed as a drug carrier for therapeutics by an equilibrium adsorption technique. The high total recovery yield of mesosilicalite (with hierarchical pores: meso and micropores) showed high stability of mesosilicalite in loading of antioxidant at high acidic pH condition (pH ~3). The lower total recovery yield of commercially-available mesoporous SiMCM-41 and Q10 silica shows the dissolution of amorphous silica in acidic medium, while in case of mesosilicalite due to strong framework of silicalite assists amorphous mesopores integrity of SiMCM-41. Thus, it follows that the gallic acid adsorption capacity of the mesosilicalite increases and therefore has a huge potential to be the perfect nanocarrier to transport drugs through similar acidic tumor regions.

The invention claimed is:

1. A mesosilicalite nanocarrier comprising:
a hierarchical silicalite having a silica to aluminum molar ratio in a range of 1500:1 to 3000:1, comprising:
a mesophase with mesopores of a hexagonal structure, the mesopores having a volume in a range of 0.5 cc/g to 0.75 cc/g; and
a microphase with micropores of a microporous volume in the range of 0.05 cc/g to 0.1 cc/g;
and 10-50 wt % gallic acid relative to a total weight of the nanocarrier, the gallic acid in an amorphous state and loaded in the mesopores and the micropores of the nanocarrier;
wherein the mesopores have pore diameters between 3.2 nm and 3.7 nm, and the micropores have pore diameters between 2.4 nm and 3.0 nm;
wherein the mesophase content is in the range of 30% to 70% relative to a total weight of the nanocarrier, and the microphase content is in the range of 30% to 70% relative to the total weight of the nanocarrier;
wherein a mean pore diameter of the mesosilicalite nanocarrier is in the range of 3 to 4 nm; and
wherein a total recovery yield for the gallic acid is in the range of 95%-100% at a gallic acid loading rate in the range of 0.1 mmol/g of the nanocarrier to 1.0 mmol/g of the nanocarrier.

2. The mesosilicalite nanocarrier of claim 1, wherein the mesopores are cylindrically shaped and in an ordered hexagonal structure,
wherein the microphase has micropores with each micropore connected to its eight nearest micropores through pore openings, and
wherein the mesosilicalite nanocarrier has a structure with the mesophase being layered under the microphase.

3. The mesosilicalite nanocarrier of claim 1, wherein the gallic acid was loaded at a loading rate in the range of 0.1 mmol/g of the nanocarrier to 16 mmol/g of the nanocarrier.

* * * * *